United States Patent
Bobrowicz

(10) Patent No.: US 7,713,719 B2
(45) Date of Patent: May 11, 2010

(54) METHODS FOR REDUCING OR ELIMINATING α-MANNOSIDASE RESISTANT GLYCANS FOR THE PRODUCTION OF GLYCOPROTEINS

(75) Inventor: Piotr Bobrowicz, White River Junction, VT (US)

(73) Assignee: GlycoFi, Inc., Lebanon, NH (US)

( * ) Notice: Subject to any disclaimer, the term of this patent is extended or adjusted under 35 U.S.C. 154(b) by 0 days.

(21) Appl. No.: 12/291,267

(22) Filed: Nov. 7, 2008

(65) Prior Publication Data

US 2009/0117616 A1  May 7, 2009

Related U.S. Application Data

(62) Division of application No. 11/118,008, filed on Apr. 29, 2005, now Pat. No. 7,465,577.

(60) Provisional application No. 60/620,186, filed on Oct. 18, 2004.

(51) Int. Cl.
*C12N 1/14* (2006.01)
*C12N 1/15* (2006.01)
*C12N 15/09* (2006.01)

(52) U.S. Cl. .................. 435/69.1; 435/483; 435/484; 435/254.1; 435/254.2

(58) Field of Classification Search .................. None
See application file for complete search history.

(56) References Cited

U.S. PATENT DOCUMENTS

| | | | |
|---|---|---|---|
| 5,272,066 | A | 12/1993 | Bergh et al. |
| 7,029,872 | B2 | 4/2006 | Gerngross |
| 7,259,007 | B2 * | 8/2007 | Bobrowicz et al. ....... 435/255.5 |
| 7,507,573 | B2 * | 3/2009 | Contreras et al. ...... 435/254.11 |
| 2004/0018590 | A1 | 1/2004 | Gerngross et al. |
| 2006/0160179 | A1 | 7/2006 | Bobrowicz et al. |

FOREIGN PATENT DOCUMENTS

EP 1283265 2/2003

OTHER PUBLICATIONS

Mille et al. Identification of a New Family of Genes Involved in Beta-1,2-Mannosylation of Glycans in Pichia Pastoris and Candida Albicans. JBC vol. 283, No. 15, 9724-9736, Apr. 11, 2008.*
Cutler, Med. Mycology, vol. 39 (2001), pp. 75-86, "N-Glycosylation of yeast, with emphasis on candida albicans".
Shibata et al., Arch. Biochem. & Biophys., vol. 243 (1985), pp. 338-348, "Immunochemical study on the mannans of candida albicans NIH A-207, . . . ".
Shibata et al., Arch. Biochem. & Biophys., vol. 302 (1993), pp. 113-117, "Complete assignment of 1H and 13C nuclear magnetic resonance chemical shifts of beta-1,2-linked mannooligosaccharides . . . ".
Kobayashi et al., Arch. Biochem. & Biophys., vol. 294 (1992), pp. 662-669, "Structural study of a cell wall mannan-protein complex of the pathogenic yeast candida glabrata . . . ".
Han et al., Infection & Immunity, vol. 65 (1997), pp. 4100-4107, "Biochemical characterization of candida albicans epitopes that can elicit protective and nonprotective antibodies".
Kobayashi et al., Infection & Immunity, vol. 62 (1994), pp. 968-973, "Structural modification of cell wall mannans of candida albicans Serotype A strains grown in yeast extract-Sabouraud liquid medium . . . ".
Kobayashi et al., Arch. Biochem. & Biophysics, vol. 272 (1989), pp. 365-375, "Structural study of phosphomannan of yeast-form cells of candida albicans J-1012 strain . . . ".
Kobayashi et al., Arch. Biochem. & Biophysics, vol. 245 (1986), pp. 494-503, "Acetolysis of pichia pastoris IFO 0948 strain mannan containing alpha-1,2 and beta-1,2 linkages using acetolysis medium of low sulfuric acid concentration".
Jouault et al., Clin. Diagnos. Lab. Immun., vol. 4 (1997), pp. 328-333, "Differential humoral response against alpha- and beta-linked mannose residues associated with tissue invasion by candida albicans".
Cregg et al., Mol. Biotech., vol. 16 (2000), pp. 23-52, "Recombinant protein expression in pichia pastoris".
Choi et al., PNAS, vol. 100 (2003), pp. 5022-5027, "Use of combinatorial genetic libraries to humanize N-linked glycosylation in the yeast pichia pastoris".
Ziegler et al., Glycobiology, vol. 9 (1999), pp. 497-505, "Novel schizosaccharomyces pombe N-linked GalMan9GlcNAc isomers: role of the Golgi GMA12 galactosyltransferase . . . ".
Trimble et al., Glycobiology, vol. 14 (2004), pp. 265-274, "Characterization of N- and O-linked glycosylation of recombinant human bile salt-stimulated lipase secreted by pichia pastoris".
Suzuki et al., J. Biol. Chem., vol. 272 (1997), pp. 16822-16828, "Characterization of beta-l,2-mannosyltransferase in candida guilliermondii and its utilization . . . ".
Rosenfeld et al., J. Biol. Chem., vol. 249 (1974), pp. 2319-2321, "Genetic control of yeast mannan structure".
Shibata et al., Eur. J. Biochem., vol. 217 (1993), pp. 1-12, "Structural study of a cell-wall mannan of saccharomyces kluyveri IFO 1685 strain".
Takeuchi, Trends in Glycosci. & Glycotech., vol. 9 (1997), pp. S29-S35, "Trial for molecularbgreeding of yeast for the production of glycoprotein therapeutics".
Genbank No. P36044, Glycobiol., vol. 6 (1996), pp. 805-810, "Cloning and analysis of the MNN4 gene required for phosphorylation of N-linked oligosaccharides in Saccharomyces cerevisiae".
Mille et al., J. Biol. Chem., vol. 283 (2008), pp. 9724-9736, "Identification of a new family of genes involved in β-1,2-mannosylation . . . ".

* cited by examiner

*Primary Examiner*—Manjunath N Rao
*Assistant Examiner*—Kagnew H Gebreyesus
(74) *Attorney, Agent, or Firm*—John David Reilly; John C. Todaro

(57) ABSTRACT

The present invention provides methods to reduce or eliminate α-mannosidase resistant glycans on glycoproteins in yeast. The reduction or elimination of α-mannosidase resistant glycans on glycoproteins results from the disruption of the newly isolated *P. pastoris* AMR2 gene encoding β1,2-mannosyltransferase. The present invention also discloses novel genes, polypeptides, antibodies, vectors and host cells relating to α-mannosidase resistance on glycans.

16 Claims, 9 Drawing Sheets

FIGURE 1

```
   1 ATG AGA ACA CGA CTC AAC TTC CTG CTG CTC TGT ATT GCC AGT GTT TTG TCT GTG ATT TGG ATC GGA GTC CTC CTT ACT
   1►Met Arg Thr Arg Leu Asn Phe Leu Leu Leu Cys Ile Ala Ser Val Leu Ser Val Ile Trp Ile Gly Val Leu Leu Thr
  79 TGG AAT GAT AAT AAT CTT GGC GGA ATC TCC CTA AAC GGA GGC AAG GAT TCT GCC TAT GAT GAT CTG CTA TCA TTG GGA
  27►Trp Asn Asp Asn Asn Leu Gly Gly Ile Ser Leu Asn Gly Gly Lys Asp Ser Ala Tyr Asp Asp Leu Leu Ser Leu Gly
 157 AGC TTC AAC GAC ATG GAG GTC GAC TCC TAT GTC ACC AAC ATC TAC GAC AAT GCT CCA GTG CTA GGA TGT ACG GAT TTG
  53►Ser Phe Asn Asp Met Glu Val Asp Ser Tyr Val Thr Asn Ile Tyr Asp Asn Ala Pro Val Leu Gly Cys Thr Asp Leu
 235 TCT TAT CAT GGA TTG TTG AAA GTC ACC CCA AAG CAT GAC TTA GCT TGC GAT TTG GAG TTC ATA AGA GCT CAG ATT TTG
  79►Ser Tyr His Gly Leu Leu Lys Val Thr Pro Lys His Asp Leu Ala Cys Asp Leu Glu Phe Ile Arg Ala Gln Ile Leu
 313 GAC ATT GAC GTT TAC TCC GCC ATA AAA GAC TTA GAA GAT AAA GCC TTG ACT GTA AAA CAA AAG GTT GAA AAA CAC TGG
 105►Asp Ile Asp Val Tyr Ser Ala Ile Lys Asp Leu Glu Asp Lys Ala Leu Thr Val Lys Gln Lys Val Glu Lys His Trp
 391 TTT ACG TTT TAT GGT AGT TCA GTC TTT CTG CCC GAA CAC GAT GTG CAT TAC CTG GTT AGA CGA GTC ATC TTT TCG GCT
 131►Phe Thr Phe Tyr Gly Ser Ser Val Phe Leu Pro Glu His Asp Val His Tyr Leu Val Arg Arg Val Ile Phe Ser Ala
 469 GAA GGA AAG GCG AAC TCT CCA GTA ACA TCT ATC ATA GTT GCT CAG ATA TAT GAC AAA AAC TGG AAC GAG TTA AAT GGC
 157►Glu Gly Lys Ala Asn Ser Pro Val Thr Ser Ile Ile Val Ala Gln Ile Tyr Asp Lys Asn Trp Asn Glu Leu Asn Gly
 547 CAT TTC TTG GAC ATC CTG AAC CCA AAT ACT GGG AAG GTC CAG CAC AAC ACG TTT CCA CAA GTT CTT CCT ATT GCA ACC
 183►His Phe Leu Asp Ile Leu Asn Pro Asn Thr Gly Lys Val Gln His Asn Thr Phe Pro Gln Val Leu Pro Ile Ala Thr
 625 AAT TTT GTC AAA GGT AAG AAG TTT CGT GGG GCA GAA GAT CCT AGA GTT GTT TTG AGA AAG GGC CGT TTT GGA CCT GAT
 209►Asn Phe Val Lys Gly Lys Lys Phe Arg Gly Ala Glu Asp Pro Arg Val Val Leu Arg Lys Gly Arg Phe Gly Pro Asp
 703 CCT TTG GTG ATG TTC AAC TCC CTA ACT CAA GAT AAC AAA CGT AGG AGA ATT TTT ACC ATT TCT CCA TTT GAC CAG TTC
 235►Pro Leu Val Met Phe Asn Ser Leu Thr Gln Asp Asn Lys Arg Arg Arg Ile Phe Thr Ile Ser Pro Phe Asp Gln Phe
 781 AAA ACA GTC ATG TAC GAC ATT AAA GAC TAT GAG ATG CCC AGG TAT GAA AAG AAC TGG GTC CCA TTT TTC TTA AAA GAC
 261►Lys Thr Val Met Tyr Asp Ile Lys Asp Tyr Glu Met Pro Arg Tyr Glu Lys Asn Trp Val Pro Phe Leu Lys Asp
 859 AAT CAG GAG GCA GTT CAT TTT GTT TAC TCT TTC AAC CCT CTG AGA GTA CTC AAA TGC AGT CTT GAT GAC GGC TCA TGT
 287►Asn Gln Glu Ala Val His Phe Val Tyr Ser Phe Asn Pro Leu Arg Val Leu Lys Cys Ser Leu Asp Asp Gly Ser Cys
 937 GAT ATT GTG TTT GAG ATA CCG AAA GTT GAC TCC ATG TCG TCT GAG TTG CGT GGT GCC ACA CCT ATG ATC AAT CTT CCT
 313►Asp Ile Val Phe Glu Ile Pro Lys Val Asp Ser Met Ser Ser Glu Leu Arg Gly Ala Thr Pro Met Ile Asn Leu Pro
1015 CAG GCA ATT CCG ATG GCG AAG GAC AAA GAG ATC TGG GTT TCA TTC CCC AGA ACG AGA ATT GCA AAT TGT GGT TGC TCC
 339►Gln Ala Ile Pro Met Ala Lys Asp Lys Glu Ile Trp Val Ser Phe Pro Arg Thr Arg Ile Ala Asn Cys Gly Cys Ser
1093 AGG ACG ACA TAC AGA CCA ATG CTG ATG CTC TTT GTC AGA GGT TCA AAT TTC TTT GTT GAA CTC TTG TCC ACC TCT
 365►Arg Thr Thr Tyr Arg Pro Met Leu Met Leu Phe Val Arg Glu Gly Ser Asn Phe Phe Val Glu Leu Leu Ser Thr Ser
1171 CTT GAT TTT GGT CTG GAG GTT TTA CCG TAT TCA GGA AAC GGA TTA CCA TGC AGT GCG GAC CAT TCC GTT TTA ATC CCA
 391►Leu Asp Phe Gly Leu Glu Val Leu Pro Tyr Ser Gly Asn Gly Leu Pro Cys Ser Ala Asp His Ser Val Leu Ile Pro
1249 AAT AGC ATT GAT AAC TGG GAA GTC GTA GAT AGC AAT GGA GAC GAT ATC TTG ACA TTG TCA TTC AGT GAG GCG GAC AAG
 417►Asn Ser Ile Asp Asn Trp Glu Val Val Asp Ser Asn Gly Asp Asp Ile Leu Thr Leu Ser Phe Ser Glu Ala Asp Lys
1327 AGT ACC TCT GTG ATT CAT ATC AGA GGG CTG TAT AAC TAT CTA TCT GAA CTG GAT GGC TAT CAA GGT CCA GAA GCA GAG
 443►Ser Thr Ser Val Ile His Ile Arg Gly Leu Tyr Asn Tyr Leu Ser Glu Leu Asp Gly Tyr Gln Gly Pro Glu Ala Glu
1405 GAT GAA CAT AAT TTC CAG CGT ATC CTG AGT GAC TTA CAT TTT GAC AAC AAA ACC ACG GTA AAC AAT TTT ATA AAA GTA
 469►Asp Glu His Asn Phe Gln Arg Ile Leu Ser Asp Leu His Phe Asp Asn Lys Thr Thr Val Asn Asn Phe Ile Lys Val
1483 CAA TCA TGT GCA CTA GAT GCT GCC AAA GGT TAT TGT AAA GAA TAT GGG CTT ACT CGT GGG GAG GCA GAA CGA AGA AGG
 495►Gln Ser Cys Ala Leu Asp Ala Ala Lys Gly Tyr Cys Lys Glu Tyr Gly Leu Thr Arg Gly Glu Ala Glu Arg Arg Arg
1561 AGG GTC GCT GAG GAG AGA AAG AAG AAG GAG AAA GAG GAA GAA GAA AAA AAG AAA AAG AAA GAA AAA GAA GAA GAA GAG
 521►Arg Val Ala Glu Glu Arg Lys Lys Lys Glu Lys Glu Glu Glu Lys Lys Lys Lys Glu Lys Glu Glu Glu Glu
1639 AAA AAG AGG ATT GAA GAG GAG AAG AAG AAG ATT GAA GAA AAG GAA CGA AAG GAG AAA GAG AAA GAA GAA GCG GAG AGA
 547►Lys Lys Arg Ile Glu Glu Glu Lys Lys Lys Ile Glu Glu Lys Glu Arg Lys Glu Lys Glu Lys Glu Glu Ala Glu Arg
1717 AAA AAG CTG CAA GAA ATG AAA AAG AAA CTT GAG GAA ATC ACA GAA AAA CTT GAA AAA GGC CAG AGG AAT AAA GAG ATA
 573►Lys Lys Leu Gln Glu Met Lys Lys Lys Leu Glu Glu Ile Thr Glu Lys Leu Glu Lys Gly Gln Arg Asn Lys Glu Ile
1795 GAT CCA AAA GAG AAG CAA AGG GAA GAA GAA GAA AGA AAG GAG AGA GTC AGG AAA ATA GCG GAG AAA CAA AGG AAG GAG
 599►Asp Pro Lys Glu Lys Gln Arg Glu Glu Glu Glu Arg Lys Glu Arg Val Arg Lys Ile Ala Glu Lys Gln Arg Lys Glu
1873 GCG GAA AAG AAG GAG GCT GAA AAA AAG GCA AAT GAC AAA AAG GAT CTA AAA ATA AGA CAG TAG
 625►Ala Glu Lys Lys Glu Ala Glu Lys Lys Ala Asn Asp Lys Lys Asp Leu Lys Ile Arg Gln •••
```

FIGURE 5

```
1   R-------------------------------TP......CIAS..S----  AMR2p
1   ------------------------------..PQ..KFYS.R..G------  AMR1p
1   R-----------------------------R..V.....TAGA.-------  AMR3p
1   K---------------------LDTQQISH..SR..YH..-PR---------  AMR4p
1   TKSYMPLFR-----SP--RQFKKIYFI---LIPLI.AVI..HV.-----DG   CaORF1
1   -KPPKLRER----TVYWAVLT---------...PTII...FQYKEHN       CaORF2
1   LAWLRHRIRSYNTSTYSSILPSASFGKVYKIGTK...T..A.CLI.----    CaORF3
1   GN-YKPSIKQYVVTV--KAIKSSQFGRLGICAVV...V.GYPFYFIS--NNP  CaORF4
1   .Q-------------------KQYRFAPKSI.TFV..I..AI-------    CaORF5
1   ---KLEMSSYLHKVPNTGITNLSNSKS-------IV.IMFCATLLFIITSSR  CaORF6
1   LIVFHSFFSFFPPLTFFFLY----PINRDLPI.IED.I.IEDSEMFE-SDLS  CaORF7
1   DKFIQSFSHQYLDSS-SSLKLTARRKRKLTILG.PI.S..SI.IIISYSNNN  CaORF8

18  -----V...VI.----------TW..NNLG..S.-NG---GKDS.Y-----   AMR2p
18  -----QVA---TI.LA.F.PI.YI.TPSTVI.S.SWE.--A.VPTVF----   AMR1p
18  -----.M---FA..F-------..D..IPG.T.T-PG--HAVAS.Y----    AMR3p
23  --RKI..-C.SLG..LLLIVA.SHQRIRST.LHRT.--ISTI.VI----    AMR4p
39  FNKIS--EYSPTFISNR...HQDQQQKSE.L..DV.SSYF-S..V.K.PDNR CaORF1
35  SHRVQP.VLIPKA.PSL..S------..TQNE.LV.IK--------        CaORF2
49  --------CSVF.NY.Y.ADNR.LDT..IG..EENV..DRKV..I..PE-    CaORF3
49  FDTSIRYQYVDPYNDTTRKYTTIEKQHT.IGGN.TTILY.KL.QLDQTALSQL CaORF4
25  --------VV.ISTSSLVC.EESLDPIEV.D.IKK--HDRKV..I..FQ--   CaORF5
44  YLTGSESLGQIPSEIPKSSEQLNEELSQQIN.FLHK.ASFDKFNS.LLNKHM  CaORF6
49  FYSAL.I.LCCP.SI..KKFPIK.YTGAN.V.LFLQCLIA--ILNLNILYSFI CaORF7
53  ILPGLSGISISST.SDYYS.PKQQNR.EQQIQDHQTTR.GKRTI..R.FNHV  CaORF8

46  I.L-LSLG---------------SF..ME..IG.VTNI.D-------       AMR2p
57  NESYLDSL---------------QF.I.D.FLSI.NG--------         AMR1p
47  DSS-V.LG---------------TF..ME.DG.VTNI.D-------        AMR3p
65  SQEVI.-A---------------D.HPT.LTGFI..DSD-------        AMR4p
89  VEFVNE---PKNSKWIQYFGDS-------KTV.SNYIT.C..NHS.GL      CaORF1
68  --------LLKNCQIIRSYHTGYEE----TR.LGQE.QSNFHKFNPTV      CaORF2
91  ----------ITDKNLLEYYLKTLEEPLHPQDTT.RNRFIYKV.DVS.SQT.NL CaORF3
102 LN--T.--ETTNPFVQYIGNS--------SS.APSQL-.C.LVNHS.QV     CaORF4
65  --------SANNKLADFLTEAFGQRLNKGDIV.KNRDTYEI.Q.V.WNT.DL  CaORF5
97  K.DIYGLMT---------LETPTDPLP-------YLEN.NEEE.SQQNYPI   CaORF6
100 NSL/TI.LGHDGSSANTL.TIDPITTTQQQGHVE.TF.R.SG.TFKNQV----- CaORF7
106 H.HKGSYMMKDSELVKYYVETMEQALDPEDLI.RNRPTYKI.T.IP.BQK.EM CaORF8

69  -----------A..V..Q..P.S.H.T.K.TI.HD.A----C.I-E...AQI. AMR2p
81  -----------RIS-.DS.P..K..VKI.T.KP.----C.M-AY..RKIP    AMR1p
70  -----------A..V..Y.P..H.T.R..T.HEIL---C.M-..T.ARV.    AMR3p
98  -----------DS--I.A..F.E.VIYSTD.LV.H---DS.I.I..SL.     AMR4p
128 Y.SSTV-----RI.ASS.K.II.ERSF.IT.YRT.HDT.Y.LATTLSYQ.EN  CaORF1
105 .SMKPIGLDLEQ----QI..F.SQV.NDA..MA.HDI..C.LLQ.IRH      CaORF2
136 .GLSQ-------SQSSK.G..E.VSF..GF..KNC.IY.I.G..LN..E     CaORF3
138 .DPFS---------NSDI.S.IMTETQ.TI.QNIIIKESFEIMVKRLMHQ.DT CaORF4
110 .QSIGE-----K-IN.K.C.KIP--LNF.I..IY.KNA.I.YI..RI.KNEK.F CaORF5
132 .Q.........MFPSKIKLT..I.PA..QQ..GVLNNMRPY             CaORF6
147 ----------ATKN.I.DSIV.DQI.DLQVS.AV.LNKPE.D-..T..N.KLN CaORF7
159 .DGGGGGQDTSDSNTDM.PK..TTIKV.A.PAM.KNG.D.M..RKT.LQED.F CaORF8
```

FIGURE 5 CONT.

```
105 DIDV SAIKD    ED   KA  VKQKV  KH FT YG SV FL EHD HYL RR  AMR2p
116 SSEE GVLAD    A    QD T  QR  K  PT YG SS YL EHE HYL RR  AMR1p
106  TEA AALKD    H    KK  E  EK  KH FT YG SV FL DHD HYL RR  AMR3p
121 KTQ  KDLVT    D     EKMNIDD L R YI LS SSVW   GMKA I V SR  AMR4p
175 DPA   Q LE  NDR P   I IMRGELH  IYK  G SVW   G VH   SK  CaORF1
153 GKLEY   IAP  LPE QLQ NLNI VDRF YR SG  IWL  QYNMYF  IS  I CaORF2
183     Y   ISPL   PK K M VKKE  E   QLIG  SV L  DYGV L  TS  I CaORF3
182  PA   K   AP QNK SL  RMR  YH  FYK  RTSV K DYGV L  IS V CaORF4
154     Y K  V     PD GKQ R RT  EN   QLIG SV   DYGV L  IS V CaORF5
168 HDM  VEKAKAY ISD R           E K   AG     FQ  Y VS Y CaORF6
187  LRSLNNIYD    QDN   DEV     IL RK YK CG  AV  DKY   YF VN  I CaORF7
212      YR   P   PD KK FD DT   K  YC  IG  TVW  DYGVHL VS  I CaORF8

153  F AE        VT  IIV   IYD W   N HF   DI N  NT         AMR2p
164 LF      RADTPV SL  V Q YD  W   TPHT   EIVN  T  N         AMR1p
154 V  GEGN   R IT   L  G IYD W  I N HF   N LN NT           AMR3p
168 M LG NGRS   LV  FVR Q    PD    KDIA   KF   KPD  T        AMR4p
225  Y QQ    DP Q SLLY  VY  EN  I NDI   IV V NPNGE         CaORF1
205 A SPH VN  P V  T  G    RI   V KM IN  V SNDPS NGGHDS     CaORF2
230 F  ST D VK  VS  T V  V  HE R I ENV LIV    GEG           CaORF3
232  Y QK N  D   SL  T I Y   Q   TNTD L SMQDITGE          CaORF4
201  Y   N   VQ V S  SY   A  RN  EI KV  I VM  SGKA           CaORF5
211 L  PN  VA HAFA  FL  Q  L SD KE PSHT   DI FEQ EANSIFKIFKPK CaORF6
238 A    K TR N  T   V AG  V DR   IE  T KK FPFSGLE          CaORF7
259   TEK DQGS KF S A   VF  R  KEI  D  EL IV D  ENISTTNNKN KNK CaORF8

195        QHN      G V H    IA    TNFVK KK   G  EDP  V R       GRF   P AMR2p
206        TPC   P  LIH     P    IEWSVDDKWK  EDP  VF  KP        TCVS AMR1p
196        LQHHA   G V H    IA    VNWDRNSKYR  EDP  V RR         GRF   P AMR3p
210        V    I   Y L     D    I R   S WLG E A  AVNP         ET   P  AMR4p
268   RV YD  KY   VA  F   Y  SEYIKS  YGPE    LI  T           F D  CaORF1
253       FRIIS    F  I F  W DIDN  D NY  PEDP L L R           Q G  E CaORF2
271       Y PM Y   FL MS   Y H  QQ GRFY   EDPR TLVR           NKLGY  CaORF3
275   YK LEKL     PL M F  Y P L  KG  YG E   R MLV            C DME CaORF4
243       F    SY S   I PV  Y N VNQQR  K Y  EDPR MLVR         I EGY E CaORF5
264 QKYANFRNS Y P  L PI  FD KI  L  KKYY GPEDPR L RS          P CF  CaORF6
277           P TIL HYID   EG  AEKVIL  EDP  V  HEYTNE GIRIQ CaORF7
309 KPYG Y  VLY  TIA  I V  Y N S   GGRFY  EDPRIVL          TRHG E CaORF8

234 D      M       S    QD KR                   RI TISP D          AMR2p
246  I    N  L QSS   GK                        GM  TSP R S         AMR1p
235 D     M       T   QN NKL                    RI TISP D          AMR3p
244 D  V F   M QN VN                            A YGFYP RPE         AMR4p
313  RV   EN Y   QIK MSTED   DNNVHTKFEFY RS  VG   FQYQLG  LNTDG CaORF1
296  PI   E   Y  KFVHYDD  EDSIMGQTVKFQ   RSM MC  WQ Q S  SNVEG CaORF2
314  I IVY   H  KI D KS NDG   ESNIHFKAYRS   MA  LW N KG  NNVEE CaORF3
320     Y NS Y H Q IANHTTTGKTDGSVELNFEFY RS  FVG P RYQLG SNTDG CaORF4
286  PI IVYNSFNRS PPN Y LEEI   KNLVKLDTY RS  MA  IWR QLG SNVGS CaORF5
313  PL IV NMKGLR L K               IV YSYL F SNT            CaORF6
318  PL IA NA LST   EVDWK             A  HIYR LHDP           CaORF7
356  P VL TYNSH  KISEKHF  NDQ   EGKINFNNY RSL  IG IW   QLG  IHLEE CaORF8
```

FIGURE 5CONT.

```
260 ----------------FRTVMYDIKDYEMGRYEKNLVPFFKINQEA---------- AMR2p
273 ----------------DKVNLIDIEDKDRENSEKNLSPFFIDEVEVSK--YST--- AMR1p
261 ----------------YRTVMYRTNAFKMQTIEKINLVPFFIKLDQES-------- AMR3p
269 ----------------MHQVLFSIKDEEPRIKERIMTPHFVPGSPTT--------- AMR4p
364 IQDS--KFNNVTFDIKVAEIRKRGNEFTSIEKIMTPFIDELEKNQISYYGNHNL   CaORF1
347 T--SNPEYDNKVYIRVIEIKVKLLADMKSQHWTPFISELSTNI---F-------   CaORF2
365 I--ETGKMKNRVYVISHEIIKPANKFEDKERIMAPFINYQQRIQQGF------   CaORF3
373 FVDD--RFDNVKFTRMAEIKIHMQTIASIERIMTPFVDPSEEDP---------   CaORF4
337 SLPDLATTDDHKYVKVNELSLPNIKRFITERINTPFVINEDQKIQGY------   CaORF5
341 -------------EILKKRREPFANIEKIMTPEKSVAIPSIT----------   CaORF6
346 -------------HRIIRLSIEKYAPREKEKIMAPFDGNN-----------   CaORF7
407 -LPN-NEFKKNEYIKNIKFFVKFNNFGRIEKNMALFINYNGRINQGF------   CaORF8

291 ----VEFVYSFEPIRVLRGSLID----------CSQDIVFLIP-EVDSISSE- AMR2p
308 --GYVEFVISPIPLIVIRCSLFT----------CAERMIYFSP-EEGRFGLE- AMR1p
292 ----VEFVYSHIPIRVINCSLDN----------CAGDVLFEIP-HFGISGE- AMR3p
300 ----VNIVEDLQKITILRCSIIT----------CICEKEIVSG-DFGQNHGIG AMR4p
415 GKNYVLIVKQWNHLKILKEEDAFIDSS----HSTGTMFIKDVETTQE---VC CaORF1
390 -DSYIKFVIRWANIDVLRGSILGDVAGD----CVFDYRLIETLVPQNKVC CaORF2
410 -DEHVKIMKQFQDLKILKCSILDE--ED-----CVMEYQFNDK---NGA-G CaORF3
415 EIKSLIIVMQWDKIRTLKQDISNLVTDDGFIHYSAGR--EKQITHDEIEKMC CaORF4
384 -DSHLKIIISMQDISILKCSIWDA--GN----CIMEYRMNNI---KTKIS CaORF5
370 -QTTIHKIISMIPIEVIAGDI----DSGL----C--DILQKPAKHDFNYMC CaORF6
374 ----LNFVNKI-PIRILRCNINN----------GDCQKVSGHIFNIKSHENAC CaORF7
452 -ESHVELANQLKNIRILRGSIILDNDDD----GEIEFQMEDY---EDA-G CaORF8

328 -LRKAIPMINI----------FQAIPMAKI----KIIMSIPRIFRIANCL AMR2p
347 -LRKAIPMAKI----------IVHLSLPKG----KSVMNAIPRIFIRDCG AMR1p
329 -LRKAIPMLDI----------FQAIPMADI----KITMVSIPRIRISDCG AMR3p
338 IFRGISNLVPF----------ITSFT--I----IDVMVGFPKTIMESCG AMR4p
461 EVRGGTEIMWPIK-IDNNNNNNNNLNEDDISTNQEPQQQRQLMIGILRAFVKDCG CaORF1
435 PIRGGTELVNLIRQVIPRSVYHRL----------LPSHRKIFICIANTHIDNCG CaORF2
449 RLRGGTELVNINQLLTTFDHPEIK----RVKILMPQNRFIMIGVAIAAIERGG CaORF3
466 PIRGGTKIIPTI-INN--------------QLMVGFTRVIIDKCG CaORF4
424 ELRGGTFMIVNQLLDKYNFAGLE----TVKIQF-KGIEVMISFAIAALMKGG CaORF5
410 GLIGGGIQLVSIP-------LNETIPSEIRAILPIPKNRQVYICWARIFINNCG CaORF6
412 KIRGGINAIEI----------ESQ-ELPKHL-RSRKYAFGIAISEITDGG CaORF7
493 VLFGGTEIININQLLHQYDYPELN----SIKELIPNGRIYIVGFABASIKNCG CaORF8

363 CSRITYRBMLMLFIR--EG--SNFF--VELLSTSLDFGLEVLIYS-G------ AMR2p
382 CSRITYREVLTLFVI--EG--NKFY--TELISSSIDFHIDVISYD-A------ AMR1p
364 CSEIIYREMLMLFIR--EG--TNFF--AELLSSSIDFGLEVIIYT-G------ AMR3p
371 CSGHIVRIYIMVIIR--KG--DFYY--KIFVSTPLDFGIDVRSIESA------ AMR4p
513 CGSIIYRPNFLIIELN-SK------FKITYILGSINFNVSIYGLAN------- CaORF1
478 CGKVIYRPNLIVILVKDAADKT---YYKISHISSSLSIDVPIIGINV----- CaORF2
498 CCDKIYRPTIVILLKIGDDQ-----YRISHVSPFVGLGILILPV-------- CaORF3
497 CEKAIDRPEMGVLQRTDMGT-----FQVAYISFYISINIAVPGIKT------ CaORF4
472 CGSIIYRPIFTVIVIQGG-R-----FQISFVSGYMDFGVPILPV-------- CaORF5
456 CGDIIYRPNFITLVEIYDDVTDKYYYKIGDISGYFDFAAKIEFVSKQVLDEEG CaORF6
450 CVGELYREHLTLISRNKKS--DQYE--INYVGDILDFNVNPEPVTPG------ CaORF7
542 CGSRIYRPNLIVIMKIGKN------YKFAYVSSFVGLGIEILPV-------- CaORF8
```

FIGURE 5 CONT.

```
403 ---NGLPCSADHSVLIPNSIDNMEVV------LDSNGD--DILTLSFSEADKS AMR2p
422 ---KGESCSGSISVLIPNGIDSWDVS------KKQGGNSCILTLTLSEADRN AMR1p
404 ---DGLPCSSCQSVLIPNSIDNKEVT------GSNCE--CILSLWFSEALKS AMR3p
412 ---ESTSCQTARWLAVASISNWLL------DDGLDF-DYMIITLSEAIVV AMR4p
553 --YDVVCAGHEANALIPNGISMFEQ-------------DDDYLTISMIVALQD CaORF1
521 --YIPDDLCFDSMVLIYSVSWNITSLELDIEGGRWVSNLQLTLTLSISDSI CaORF2
537 --WPDKGLCDGNILEIPNGISSVHLNK-D-----EDNSVQDYLTISISRADSI CaORF3
538 --HEIQCGKRDPNVLIPNGISNIEVPTID-------CIERVVLIMFLSAAIED CaORF4
510 --ARGRGLCNGNILIPNGISNWVLPK-D-----EGGCFQDYMILSLQRSDSI CaORF5
509 NLYEKAEQCQGRNVLIPISIAYWDVGSIKLAGTEYQKHDFKDMFSSGKVSCFN CaORF6
493 ---IT-TCSDGKSVLIPISVAF---------------IDDYMSVIFSEADKI CaORF7
580 --YLDKGLCEHYNLIIPNGISSITIEK-DLHQKEKDKQVMDYMAFIISRRLAI CaORF8

444 TSVIFIRGIYNVLSEIDGYQGPEAEDEHNFQRILSDLHFDNKTTVNFIKVCS AMR2p
465 TVVVFVRGLIDALIVINN-EGP-IHDSHSFKNVLSTNHFKSDPTELNSVRAAE AMR1p
445 TSVVHIRGIYRVLSEIDGYGGPEAEDEHNFQRILSDLHFDGKKTIEFFKVCS AMR3p
454 NSVLRVRIAKFVDNITMDEGS-------------------TTLSTNNIDE AMR4p
591 NTLVHIHCVKRIIYSI-DHFWNG--ILKENKQIECVVNNAND--PCKAYADEH CaORF1
572 VHRLDIRGIFQSTIDLADRS--------------------LFIPVDRET CaORF2
582 VDLLIKGLLNSII-----------------------------GDDPNS-- CaORF3
582 NILMDIHGIKTVIKNIITNQKHGNEFNSDSVQMKCVVAYSIE--PCRAYGEQ CaORF4
555 VDIIIMREILIKSII----------------------------SE-- CaORF5
562 ANEIVFNDYMGVTLSSADRI-------VSIVHVKGLLNYILQ--I---PSLVDD CaORF6
527 NKLINAKGWITYITKMLEFTQERLKDE-----------SSDPVLESRLLSK CaORF7
630 VDVNYVKGLLRA-I-------------------------GTDSSSSK CaORF8

497 CALDAAKGYCKEYGLIRGEAERR-RRVAEERKKKIKEIEEKIKKKIKEEEEKK AMR2p
516 CIIFSSRDYCKKYCEIRGEPARYAKQMENERKEKIKKEI---KIAKIKLEAEKA AMR1p
498 CALDAIKIYCKEYIVIRGEEDRL-KN-----KEKIRKIEEKRKK----ELERK AMR3p
487 CIITTGSKDYCQRYI---------------------------------- AMR4p
639 YKIGDSEI---AIKEVQKA-KEEAEKAKAEKIKAIKEKAIKEKAEINKAI CaORF1
601 RVIIEFIN-----GLCIPGSNPLNQDVNSLGVNNDWIVCILDAIVEILFEYCA CaORF2
602 KLIELNDY-----IFNI------------------KNIECAVISIDAFCIKIGS CaORF3
633 ARIG------------------------------------------------ CaORF4
571 YLIQTNRD-----VINI-----------------NAIHCILLISESYCISWAE CaORF5
604 SLVINKEW-----TFQK-------------KGHDLIVRCIMIAIKIYCISWAI CaORF6
567 ISTFLICQYC---AISKDTMGW------------------------------ CaORF7
651 HLIAVECT-----IGFKSV----------------TIVDCALINIEKFCIIYGI CaORF8

549 RIEIENKIIBEK-ERKEKEKEEAIRIKLQEMKKKLEEITIEKLEIGQRNKEIDP AMR2p
566 EMEIAVRIAQEAIAQKEREKEEAIQEKKAQQEAKEKEAFIKAAIEKEAKENEA AMR1p
541 NKEIENKIKEEE-EKKKKEEEEEIEIRLKELKKKLKELQIEEEI-QKDEVKDT AMR3p
501 ---------------------------------------------------- AMR4p
686 NEKIEINEIE--EKEEKEKAEKERIEIEKAEKELAEKELAIQKDEDAKDEDKNE CaORF1
649 KFSIPIKQEEFYEVEQQEFNEELIDPIKHQYFKILGKYLYDHASVNS CaORF2
633 EYKLNNNIE---------IDIANG----------NGKGSSS CaORF3
637 -----------------------------LTGGWLPSHN CaORF4
602 NYRAHLKR-------------------------WQN CaORF5
639 I--------------------------------QGVKIDEKSE CaORF6
586 --------------------------------DIKLSR CaORF7
683 TF CaORF8
```

FIGURE 5 CONT.

```
601 KEKQREEEERKERVRKIAEKQRKEAEKKEAEKKANDKKDLKIRQ          AMR2p
619 K--------KKIIVEKLA-KEQEEAEKLEAKKKLYQLQE-EERS          AMR1p
592 KAK                                                   AMR3p
501 ---------------------------------------ELH            AMR4p
737 DEDDKEKNDESGLTEKSEVEENGENTSEGSEGEEEDDDDIEV            CaORF1
694                                                       CaORF2
654                                                       CaORF3
646                                                       CaORF4
612                                                       CaORF5
650 ------------------------------------------ET          CaORF6
590                                                       CaORF7
684                                                       CaORF8
```

METHODS FOR REDUCING OR ELIMINATING α-MANNOSIDASE RESISTANT GLYCANS FOR THE PRODUCTION OF GLYCOPROTEINS

CROSS-REFERENCE TO RELATED APPLICATIONS

This application is a divisional of U.S. application Ser. No. 11/118,008, filed Apr. 29, 2005, and now U.S. Pat. No. 7,465,577, and which claims benefit of U.S. provisional application Ser. No. 60/620,186 filed on Oct. 18, 2004.

FIELD OF THE INVENTION

The present invention relates to the field of protein glycosylation engineering in lower eukaryotes. The present invention further relates to engineering of yeast and filamentous fungal host cells for the production of therapeutic glycoproteins. In particular, the present invention relates to the reduction or elimination of α-mannosidase resistant glycans on glycoproteins, and methods for reducing or eliminating a gene involved in the production of α-mannosidase resistance on glycans in yeast cells.

BACKGROUND OF THE INVENTION

The ability to produce recombinant human proteins has led to major advances in human health care and remains an active area of drug discovery. Many therapeutic proteins require the posttranslational addition of glycans to specific asparagine residues (N-glycosylation) of the protein to ensure proper structure-function activity and subsequent stability in human serum. For therapeutic use in humans, glycoproteins require human-like N-glycosylation. Mammalian cell lines (e.g., CHO cells, human retinal cells) that can mimic human-like glycoprotein processing have several drawbacks including low protein titers, long fermentation times, heterogeneous products, and continued viral containment. It is therefore desirable to use an expression system that not only produces high protein titers with short fermentation times, but can also produce human-like glycoproteins.

Fungal hosts such as the methylotrophic yeast *Pichia pastoris* has distinct advantages for therapeutic protein expression—e.g. it does not secrete high amounts of endogenous proteins, it has a strong inducible promoter, it can be grown in defined chemical media, and it can produce high titers of recombinant proteins (Cregg et al., 2000). However, glycosylated proteins expressed in *P. pastoris* contain additional mannose sugars resulting in "high mannose" glycans, as well as mannosylphosphate groups which impart a negative charge onto glycoproteins. Glycoproteins with either high mannose glycans or charged mannans are a high risk for illiciting an immune response in humans (Takeuchi, 1997; Rosenfeld and Ballou, 1974). Accordingly, it is desirable to produce therapeutic glycoproteins in fungal host systems, such that the pattern of glycosylation is identical or at least similar to that in humans.

Some fungal hosts contain immunogenic β-mannosylation on glycans of glycoproteins. In order to circumvent antigenicity, it is desirable to eliminate β-mannosylation in the production of human-like glycoproteins. Oligomannosides with β-1,2-linkage were first described by Shibata et al., (1985) in association with *Candida albicans* cell wall phosphopeptidomannan by phosphodiester bridges. Subsequently, three types of β-1,2 linkages have been identified in the side chains of *Candida* cell wall mannans. The first is a β-1,2-linked manno-oligomer located in a phosphodiesterified oligosaccharide moiety which is a common epitope in the mannans of several *Candida* species (Shibata et al 1993a). The second type is a β-1,2-linked mannose unit attached to the nonreducing terminal of the α-1,2 oligomannosyl side chains in the mannans of *Candida albicans, tropicalis* and *glabrata* (Kobayashi et al., 1989, 1992 and 1994). The third type of β-1,2 linkage is found in *Candida guilliermondii* and contains α-1,2 linked mannose units attached to an α-1,3 linked mannose unit (Shibata et al., 1993b).

Despite these findings, the studies on β-1,2 linkages have been limited by unsuccessful attempts to identify a β-1,2 mannosyl-transferase gene. Suzuki et al., (1997) characterized the presence of a β-1,2-mannosyltransferase in *Candida guilliermondii*, however, a gene for this enzyme has yet to be cloned.

In *C. albicans* yeast, both the β-oligomannosides which make up the acid-labile region of the phosphomannan complex, and α-oligomannosides, which make up the acid-stable region of the complex, serve as adhesins in the attachment of these pathogenic yeast cells to host splenic and lymph node macrophages (Cutler, 2001). Interestingly, antibodies protective against various forms of candidiasis recognize β-linked mannotriose, but not oligomannosides of greater mannose chain length (Han et al, 1997). It was reported that patients who develop deep tissue invasion with *C. albicans*, do not have detectable antibody titers specific for β-linked oligomannosides, whereas such antibodies were present in healthy individuals (Jouault et al, 1997).

There are few examples of β-linked mannose residues on glycoproteins from *P. pastoris*. In 1986, Kobayashi et al, described a modified acetolysis method with milder conditions for the isolation of manno-oligosaccharides composed predominantly of β-1,2 linked mannose residues. In 2003, Trimble et al reported the presence of β-1,2-linked mannose residues in the recombinant human bile salt-stimulated lipase (hBSSL) expressed in *P. pastoris*. As evidenced by the presence of protective antibodies in uninfected individuals, β-linked mannans are likely to be immunogenic. Additionally, exposed mannose groups on therapeutic proteins are rapidly cleared by mannose receptors on macrophage cells, resulting in low drug efficacy. Thus, the presence of α-linked mannose residues on N- or O-linked glycans of heterologous therapeutic proteins expressed in a fungal host e.g., *P. pastoris* is not desirable given their immunogenic potential and their ability to bind to clearance factors.

What is needed, therefore, is a method for removing undesired mannose residues on glycoproteins for the production of therapeutic glycoproteins.

SUMMARY OF INVENTION

Accordingly, the present invention provides methods for producing glycoprotein compositions in yeast or filamentous fungal host cells, said glycoprotein compositions having reduced amounts of high mannose glycans, said method comprising reducing or eliminating the presence of α-mannosidase resistant glycans on said glycoproteins. In certain embodiments, reducing or eliminating α-mannosidase resistant glycans on glycoproteins is accomplished by modifying the host cell through disruption, deletion or mutation of a gene involved in mannosylation of N-glycans. Such genes may include, for example, the gene sequences described herein as SEQ ID NO: 11 or variants thereof.

In certain embodiments, the α-mannosidase resistant glycans may comprise β-mannose, branched high mannose, or α-1,4 mannose residues.

The host cells of the present invention are preferably of yeast and/or filamentous fungal origin. The host cells useful in the present invention may include the following families, genie, and species: *Pichia pastoris, Pichia finlandica, Pichia trehalophila, Pichia koclamae, Pichia membranaefaciens, Pichia methanolica, Pichia minuta (Ogataea minuta, Pichia lindneri), Pichia opuntiae, Pichia thermotolerans, Pichi salictaria, Pichia guercum, Pichia pijperi, Pichia stiptis, Pichia sp., Saccharomyces castellii, Saccharomyces cerevisiae, Saccharomyces kluyveri, Saccharomyces sp., Hansenula polymorpha, Kluyveromyces sp., Kluyveromyces lactis, Candida albicans, Candida sp., Aspergillus fumigatus, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa*.

In certain embodiments, the host cells of the present invention may comprise a deletion of a functional gene encoding an alpha-1,6-mannosyltransferase activity, such as OCH1. In other embodiments, the host cells of the present invention may further comprise a gene encoding an mannosylphosphate transferase activity, such as PNO1 and MNN4B.

The present invention also provides glycoprotein compositions with reduced amounts of high mannose glycan structures that are recalcitrant to α-mannosidase, which may be produced by the methods of the present invention. Such glycoprotein compositions may comprise either N-linked glycans and/or O-linked glycans.

The present invention further provides isolated nucleic acid sequences which are involved in the production of α-mannosidase resistant glycans. These isolated nucleic acid sequences include the sequences described herein as SEQ ID NO: 11 or variants thereof. Also included in the present invention are other nucleic acid sequences which exhibit structural similarity to the above sequences. These may include, for example, degenerate variants of SEQ ID NO: 11 as well as nucleic acid sequences having a high level of nucleotide sequence identity with the above. Nucleic acid sequences included in the present invention would therefore include those nucleic acid sequences having at least 72% 75%, 80% or 85% 90%, 95%, 98%, 99%, 99.9% identity to the sequences of SEQ ID NO: 11 as well as nucleic acid sequences that encode a polypeptide having the amino acid sequences which is produced by SEQ ID NO: 11; nucleic acid sequence that encode polypeptides having at least 72% 75%, 80% or 85% 90%, 95%, 98%, 99%, 99.9% identity to the polypeptides having the amino acid sequences which are produced by SEQ ID NO:12, SEQ ID NO:13, SEQ ID NO:14, or SEQ ID NO:15; and nucleic acid sequences that hybridize under stringent conditions to the nucleic acid sequences described as SEQ ID NO: 11. The present invention also includes nucleic acid sequences comprising a fragment of any of the above nucleic acid sequences that is at least 60 contiguous nucleotides in length.

In still other embodiments, the present invention provides modified yeast or filamentous fungal host cells. The host cells of the present invention may be characterized as having been modified to reduce expression of the functional gene products of one or more a nucleic acid sequence selected from the group consisting of SEQ ID NO: 11. In certain embodiments, the modified host cell comprises a disruption, deletion or mutation in one or more nucleic acid sequences selected from the group consisting of SEQ ID NO: 11. In other embodiments, the modified host cell comprises a cellular inhibitor of expression of the functional gene product of a nucleic acid selected from the group consisting of SEQ ID NO:11 or variants thereof. Cellular inhibitors of expression useful for the present invention include, for example antisense DNA and short interfering RNA.

In other embodiments, the present invention may comprise modified yeast or filamentous fungal host cells which are capable of expressing glycoprotein compositions having reduced amounts of high mannose glycans, said glycoprotein compositions comprising reduced presence of α-mannosidase resistant glycans, for example β-mannosyl residues.

BRIEF DESCRIPTION OF THE DRAWINGS

FIG. 1 depicts the nucleic acid (SEQ ID NO:11) and amino acid sequence (SEQ ID NO:12) of the *P. pastoris* AMR2 gene.

FIG. 5 The deduced amino acid sequence of the *P. pastoris* AMR2 gene is shown aligned with the amino acid sequence of AMR2 homologs from *Candida albicans*. AMR2p (SEQ ID NO:12), AMR1p (SEQ ID NO:13), AMR3p (SEQ ID NO:14), AMR4p (SEQ ID NO:15), CaORF1 (SEQ ID NO:16), CaORF2 (SEQ ID NO:17), CaORF3 (SEQ ID NO:18), CaORF4 (SEQ ID NO:19), CaORF5 (SEQ ID NO:20), CaORF6 (SEQ ID NO:21), CaORF7 (SEQ ID NO:22), CaORF8 (SEQ ID NO:23).

DETAILED DESCRIPTION OF THE INVENTION

Figure 2:
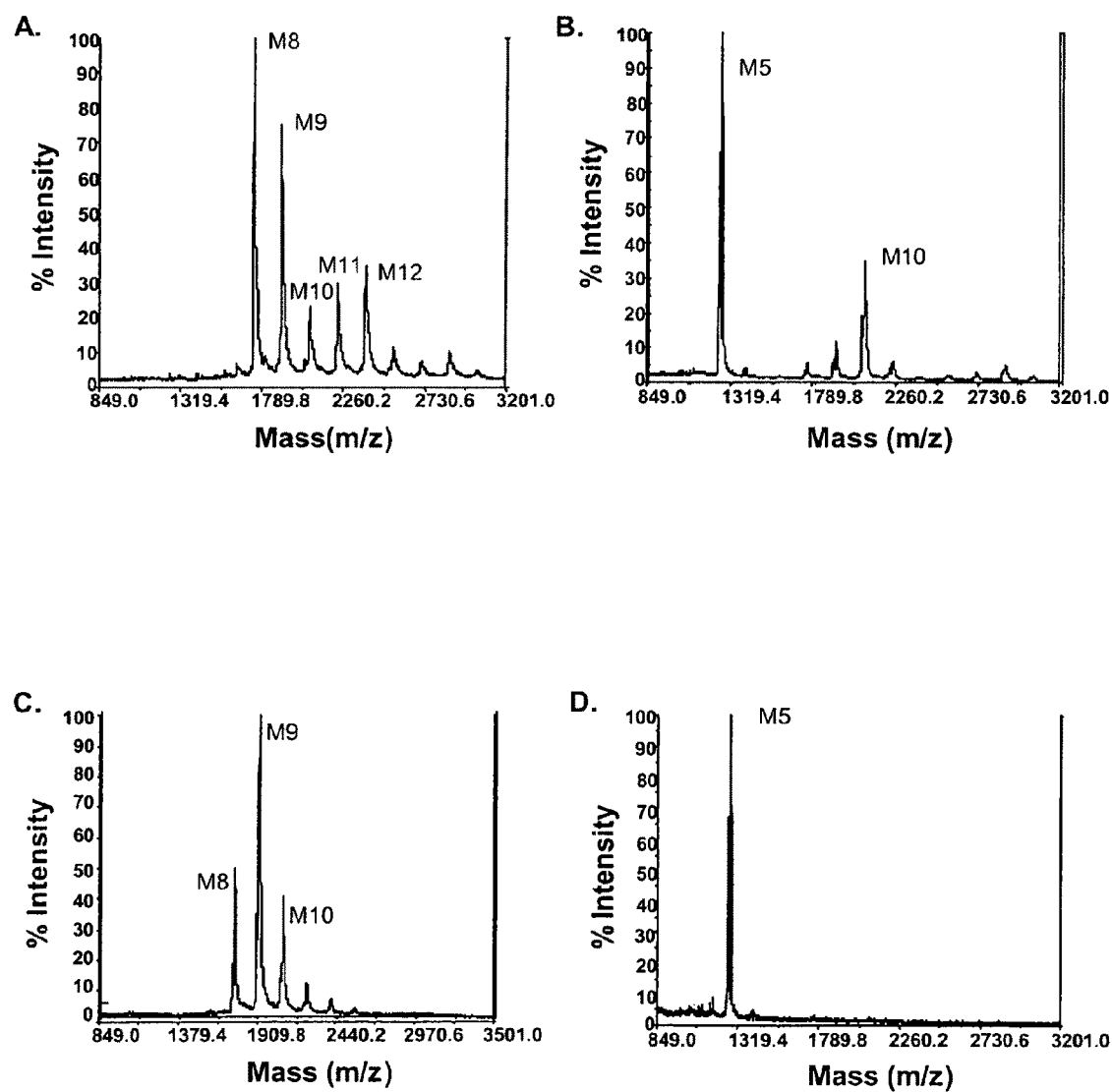
FIG. 2 A. MALDI-TOF MS showing the N-glycans of *P. pastoris* YAS137 (Δoch1, Δpno1, Δmnn4b). B. MALDI-TOF MS showing the N-glycans of *P. pastoris* YAS137 after digestion with α-1,2 mannosidase. C. MALDI-TOF MS showing the N-glycans of *P. pastoris* PBP130 (Δoch1, Δpno1, Δmnn4b, Δamr2). D. MALDI-TOF MS showing the N-glycans of *P. pastoris* PBP130 (Δoch1, Δpno1, Δmnn4b, Δamr2) after digestion with α-1,2 mannosidase.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of*

*Biochemistry. Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., Molecular Cloning: *A Laboratory Manual*, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique*, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

As used herein, the term "sequence of interest" or "gene of interest" refers to a nucleic acid sequence, typically encoding a protein that is not normally produced in the host cell. The methods disclosed herein allow one or more sequences of interest or genes of interest to be integrated into a host cell genome. A preferred integration site is the AMR2 locus. Non-limiting examples of sequences of interest include sequences encoding one or more polypeptides having an enzymatic activity, e.g., an enzyme which affects N-glycan synthesis in a host such as mannosyltransferases, N-acetylglucosaminyltransferases, UDP-N-acetylglucosamine transporters, galactosyltransferases and sialyltransferases.

As used herein, the term "therapeutic glycoprotein" includes erythropoietin, cytokines such as interferon-α, interferon-β, interferon-γ, interferon-ω, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon-like protein 1, IL-2 receptor agonist.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities. The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab')$_2$, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., *Intracellular Antibodies: Research and Disease Applications*, (Marasco, ed., Springer-Verlag New York, Inc., 1998), the disclosure of which is incorporated herein by reference in its entirety).

As used herein, antibodies can be produced by any known technique, including harvest from cell culture of native B lymphocytes, harvest from culture of hybridomas, recombinant expression systems and phage display.

The term "non-peptide analog" refers to a compound with properties that are analogous to those of a reference polypeptide. A non-peptide compound may also be termed a "peptide mimetic" or a "peptidomimetic". See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W.H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 65% overall sequence homology to its wild-type counterpart. Even more preferred are muteins having at least 70%, 75%, 80%, 85% or 90% overall sequence homology to the wild-type protein. In an even more preferred embodiment, a mutein exhibits at least 95% sequence identity, even more preferably 98%, even more preferably 99% and even more preferably 99.9% overall sequence identity. Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) In a preferred embodiment, a homologous protein is one that exhibits at least 72% sequence homology to the wild type protein, more preferred is at least 75% sequence homology. Even more preferred are homologous proteins that exhibit at least 80%, 85%, 90% or 95% sequence homology to the wild type protein. In a yet more preferred embodiment, a homologous protein exhibits at least 96%, 98%, 99% or 99.9% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred Parameters for BLASTp are:

Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least twofold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

The term "high mannose" as used herein refers to a glycan structure on a glycoprotein which is natively produced by species of yeast and/or filamentous fungi, and generally has eight or more mannose residues.

As used herein, the term "molecule" means any compound, including, but not limited to, a small molecule, peptide, protein, sugar, nucleotide, nucleic acid, lipid, etc., and such a compound can be natural or synthetic.

The terms "α-mannosidase resistant glycans" and "recalcitrant α-mannose glycans" are used interchangeably herein and refer to glycan structure of a glycoprotein which are wholly or partially resistant to cleavage by alpha-mannosidases, such as with α-1,2; α-1,3; and/or α-1,6-mannosidases. Recalcitrant α-mannose glycans may include β-mannose, branched high mannose, α-1,4 mannose or uncharacterized mannose. These glycan structures therefore contribute to increased presence of high mannose glycan structures.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Identification of α-Mannosidase Resistant Gene

In an effort to express human-like glycoproteins in fungal systems, elimination of non-human glycosylation is desired. Fungal glycosylation is characterized by high mannose/non-human glycans. Determining the type of mannosylation is commonly the first step in eliminating undesired glycosylation events. The deletion of OCH1 in *P. pastoris* led to a decrease in hypermannosylation (Choi et al., 2003). Analysis by negative MALDI-TOF MS, revealed the presence of negative charges associated with these mannose groups. The subsequent deletion of the putative mannosylphosphate transferase genes, PNO1 and MNN4B, led to a strain devoid of mannosylphosphate (FIG. 2A) (U.S. Pat. No. 7,259,007). Digestion of the remaining mannose groups by α-1,2 mannosidase and Jack Bean mannosidase further reduced the size of the mannans (FIG. 2B, FIG. 3) (Example 1). Despite these gene disruptions and digests with α-mannosidases, up to 20% of the N-glycans remained resistant. From sugar composition analysis, and the resistance of these mannose groups to α-1,2 mannosidase and Jack Bean mannosidase (α-1,2/α-1,3/α-1,6) it was deduced that these mannose structures are branched β-mannose, high mannose, α-1,4 mannose or uncharacterized mannose.

It was initially postulated that these resistant mannans result from mannosyltransferase activity, and it was thus speculated that the gene (or genes) responsible for these resistant mannans would have some homology to other mannosyltransferase genes. A C-terminal sequence from the *Saccharomyces cerevisiae* MNN4 gene was used to probe the *P. pastoris* genome (Example 2). By selecting genes encoding putative Type II membrane proteins (and thus, could be found on the Golgi membrane), a gene was identified that when disrupted, eliminates the resistant mannans after digest with α-1,2 mannosidase (FIG. 2D). We have named this gene AMR2 (alpha-mannosidase resistant). Accordingly, the present invention discloses a *P. pastoris* gene involved in mannosylation of glycoproteins as set forth in FIG. 1.

Nucleic Acid Sequences

In one aspect of the present invention, a gene involved in the mannosylation of N-glycans which are resistant to known α-mannosidases is identified and sequenced in *P. pastoris* (FIG. 1, Example 2). In one embodiment, a nucleic acid sequence encoding the *P. pastoris* AMR2 gene and variants thereof are provided. Disruption of the *P. pastoris* AMR2 gene is particularly useful for the reduction or elimination of α-mannosidase-resistant glycans on glycoproteins in a yeast strain. In another embodiment, the present invention provides a nucleic acid molecule comprising or consisting of a sequence which is a variant of the *P. pastoris* AMR2 gene having at least 72% identity to SEQ ID NO: 11. The nucleic acid sequence preferably has at least 75%, 80% or 85% identity to the wild type gene. Even more preferably, the nucleic acid sequence has 90%, 95%, 98%, 99%, 99.9% or even higher identity to the SEQ ID NO: 11.

According to other embodiments of the invention, the nucleic acid molecule of the invention encodes a polypeptide having the amino acid sequence shown in FIG. 1. Also provided is a nucleic acid molecule encoding a polypeptide sequence that is at least 72% identical to SEQ ID NO: 12. Typically, the nucleic acid molecule of the invention encodes a polypeptide sequence of at least 75%, 80% or 85% identity to SEQ ID NO: 12. Even more preferably, the encoded polypeptide has 90%, 95%, 98%, 99%, 99.9% or even higher identity to the SEQ ID NO: 12.

In another aspect of the invention, the AMR2 gene involved in α-mannosidase-resistant mannosylation of N-glycans is homologous to three other genes in *P. pastoris*—AMR1, AMR3, AMR4 (FIG. 5), and has regions of homology to genes in the following species: eleven genes in *Candida albicans*, (eight shown in FIG. 5); eight genes in *Saccharomyces castellii* strain NRRL Y-12630; two genes in *Saccharomyces kluyveri* strain NRRL Y-12651, and three genes in *Aspergillus fumigatus* (Example 3). For the reduction or elimination of recalcitrant α-mannose glycans in other species, a person skilled in the art can identify AMR2 homologs from the genome of a given species, and disrupt the homologous gene or genes. One skilled in the art understands that it may be necessary to disrupt all homologous genes, or a combination of homologous genes found in any given species. More specifically, a skilled artisan recognizes that in order to reduce or eliminate α-mannosidase resistant N-glycans in other species, degenerate primers from the conserved sequences can be designed for PCR cloning of AMR2 homologs. Alternatively a probe could also be constructed for hybridization of the AMR2 homologs.

Host Cells

In another aspect of the invention, a host cell producing glycoproteins, which normally has α-mannosidase-resistant glycans, has been engineered to produce glycoproteins without α-mannosidase-resistant N-glycans. In one embodiment, a host cell producing therapeutic glycoproteins, which normally has mannosidase-resistant glycans, has been engineered to produce therapeutic glycoproteins without mannosidase-resistant glycans. In a preferred embodiment, the host cells of the invention have been mutated by recombination with a disruption, deletion or mutation of the isolated nucleic acid of the invention so that the α-mannosylation on glycans in the host cell is reduced compared to a host cell lacking the mutation. More preferably, α-mannosidase-resistance on N-glycans is eliminated. The host cell of the invention is preferably *Pichia pastoris* or *Pichia methanolica*, but other host cells, especially yeast cells, are also encompassed within the scope of the invention.

Figure 4:
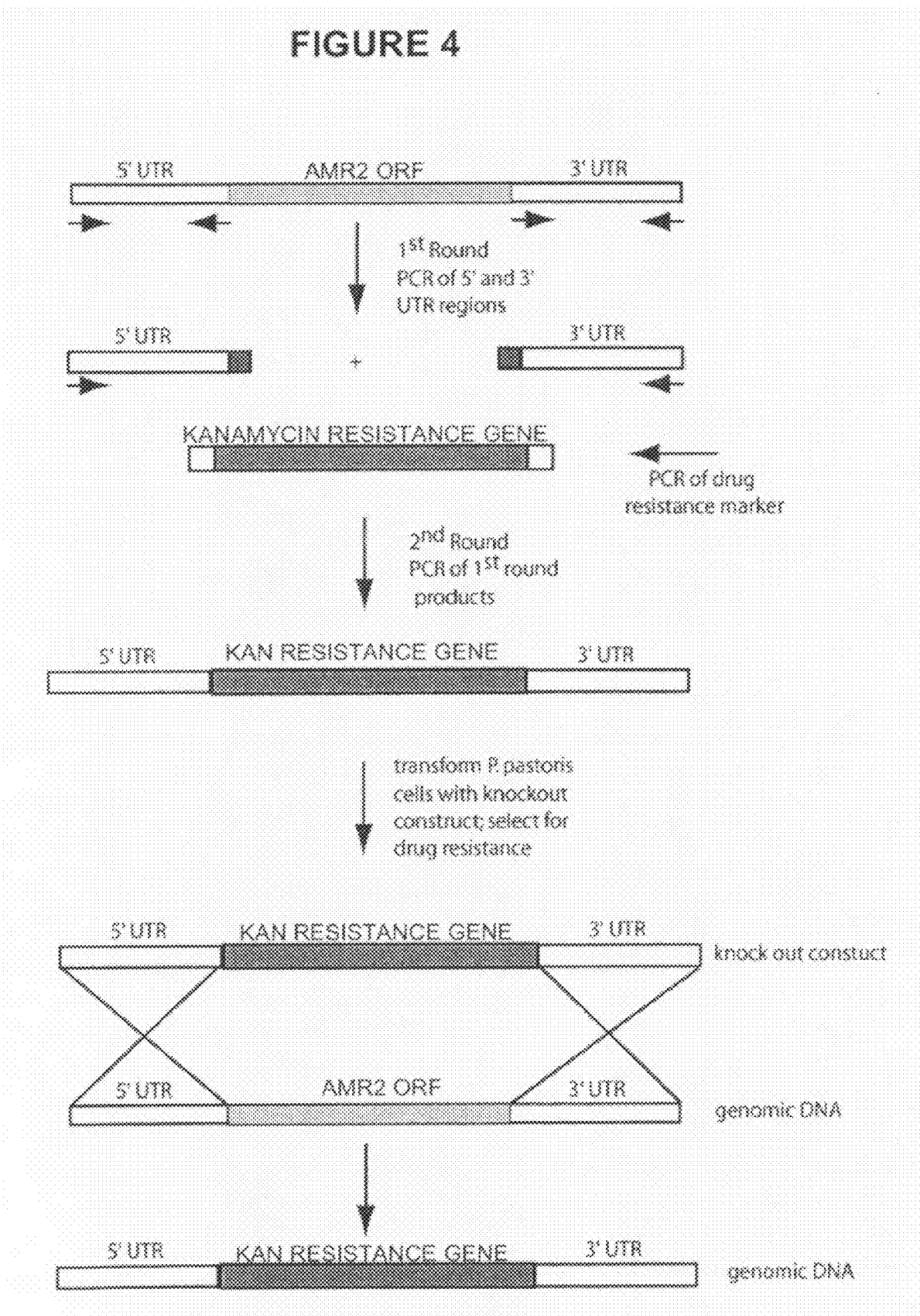
FIG. 4 illustrates the fusion PCR knock-out strategy of *P. pastoris* AMR2 using the drug resistance marker, kanamycin.

In some embodiments, the AMR2 gene in a yeast host cell is disrupted by the PCR knock-out strategy discussed in Example 3 and shown in FIG. 4. In other embodiments of the invention, host cells defective in α-mannosidase resistance activity are used to integrate one or more sequences or genes of interest into the host cell genome using nucleic acid molecules and/or methods of the invention. In a preferred embodiment, the sequences or genes of interest are integrated so as to disrupt an endogenous gene of the host cell. For example, the AMR2 gene is disrupted by a sequence of interest. Host cells containing the integration are easily identified by a selection marker, which in yeast are usually auxotrophic genes that allow growth of transformed cells on a medium lacking the specific amino acid or nucleotide or an antibiotic resistance gene, which allows for growth on media containing the corresponding antibiotic.

In another aspect of the invention, host cells transformed with the nucleic acid molecules or vectors of the invention, and descendants thereof, are provided. In some embodiments of the invention, these cells carry the nucleic acid sequences of the invention on vectors, which may but need not be freely replicating vectors. In other embodiments of the invention, the nucleic acids have been integrated into the genome of the host cells.

The disrupted AMR2 gene which encodes an activity involved in α-mannose resistance on glycans of glycoproteins is preferably from a yeast strain belonging to the genus *Pichia*. Yeasts belonging to the genus *Pichia* according to the present invention include for example, *Pichia pastoris*, *Pichia finlandica*, *Pichia trehalophila*, *Pichia koclamae*, *Pichia membranaefaciens*, *Pichia methanolica*, *Pichia minuta (Ogataea minuta, Pichia lindneri), Pichia opuntiae*, *Pichia thermotolerans*, *Pichi salictaria*, *Pichia guercum*, *Pichia pijperi*, *Pichia stiptis*, *Pichia* sp., and other yeasts, but not limited thereto. In yet another embodiment, genes carrying AMR2 activity and/or homology can be disrupted in one of the following hosts: *Saccharomyces castellii*, *Saccharomyces cerevisiae*, *Saccharomyces kluyveri*, *Saccharomyces* sp., *Hansenula polymorpha*, *Kluyveromyces* sp., *Kluyveromyces lactis*, *Candida albicans*, *Candida* sp., *Aspergillus fumigatus*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens* and *Neurospora crassa*.

AMR2 Gene Encoding β-Mannosylation Activity

It was observed that some yeast species with homologs to this AMR2 gene also have β-mannosylation activity. Accordingly, in another aspect of the invention, the AMR2 gene encodes β-mannosyltransferase activity. In one embodiment, AMR2 encoding β-mannosyltransferase activity is disrupted individually and/or in combination with any of its homologs in *P. pastoris* or other fungal species, resulting in the reduction or elimination of α-mannosylation resistant glycans on glycoproteins.

The presence of β-mannosylation on O-glycans is discussed in the report by Trimble et al, 2003. Accordingly, in a further embodiment, α-mannosidase resistant O-glycans in *P. pastoris* and other species is reduced or eliminated with the disruption of the AMR2 gene and its homologs.

The following are examples which illustrate the compositions and methods of this invention. These examples should not be construed as limiting—the examples are included for the purposes of illustration only.

EXAMPLE 1

Jack Bean and α-1,2 Mannosidase Digestion of N-glycans

The standard N-linked oligosaccharides (20 μg) was reconstituted in 100 μl HPLC grade water. A 10 μl aliquot was added to a 0.6 ml siliconized tube. The sample was evaporated to dryness. To the sample, 10 μl of 50 mM ammonium acetate was added, along with Jack Bean mannosidase (0.03 U) or α-1,2 mannosidase from *Trichoderma reseei* (0.03 mU, a gift from Dr Contreras R, Unit of Fundamental and Applied Molecular Biology, Department of Molecular Biology, Ghent University, Ghent, Belgium). The sample was incubated with the enzyme for 16 to 24 hr at 37° C. The sample was then evaporated to dryness. The sample was reconstituted in 10 μl of water. The sample was subsequently analyzed by MALDI-TOF MS.

Matrix Assisted Laser Desorption Ionization Time of Flight Mass Spectrometry Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybenzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than $5 \times 10^{-7}$ torr, and the low mass gate was 875 Da. Spectra were generated from the sum of 100-200 laser pulses and acquired with a 2 GHz digitizer. $Man_5GlcNAc_2$ oligosaccharide was used as an external molecular weight standard. All spectra were generated with the instrument in the positive ion mode. The estimated mass accuracy of the spectra was 0.5%.

EXAMPLE 2

Identification and Sequence Analysis of AMR2 Gene from *Pichia pastoris*

The C-terminal part of *Saccharomyces cerevisiae* MNN4 gene (Genbank accession # P36044) containing a repetitive sequence rich in lysine and glutamic acid was used as a probe to blast against a *P. pastoris* genomic sequence (Integrated Genomics, Chicago, Ill.). Several DNA fragments with ORF's encoding proteins with similar lysine and glutamic acid rich repeats were identified. Among those one ORF was found to encode for a protein of 644 amino acids with putative N-terminal transmembrane domain and C-terminal tail rich in lysine and glutamic acid structurally resembling *S. cerevisiae* Mnn4p. Base on the phenotype analysis of the strain carrying mutated allele, the gene was named AMR2 (alpha-mannosidase resistant). Subsequent blast searches of *P. pastoris* genomic sequence revealed the presence of three more genes closely related to AMR2.

EXAMPLE 3

Deletion of AMR2 Gene in YAS137 Strain

Figure 3:
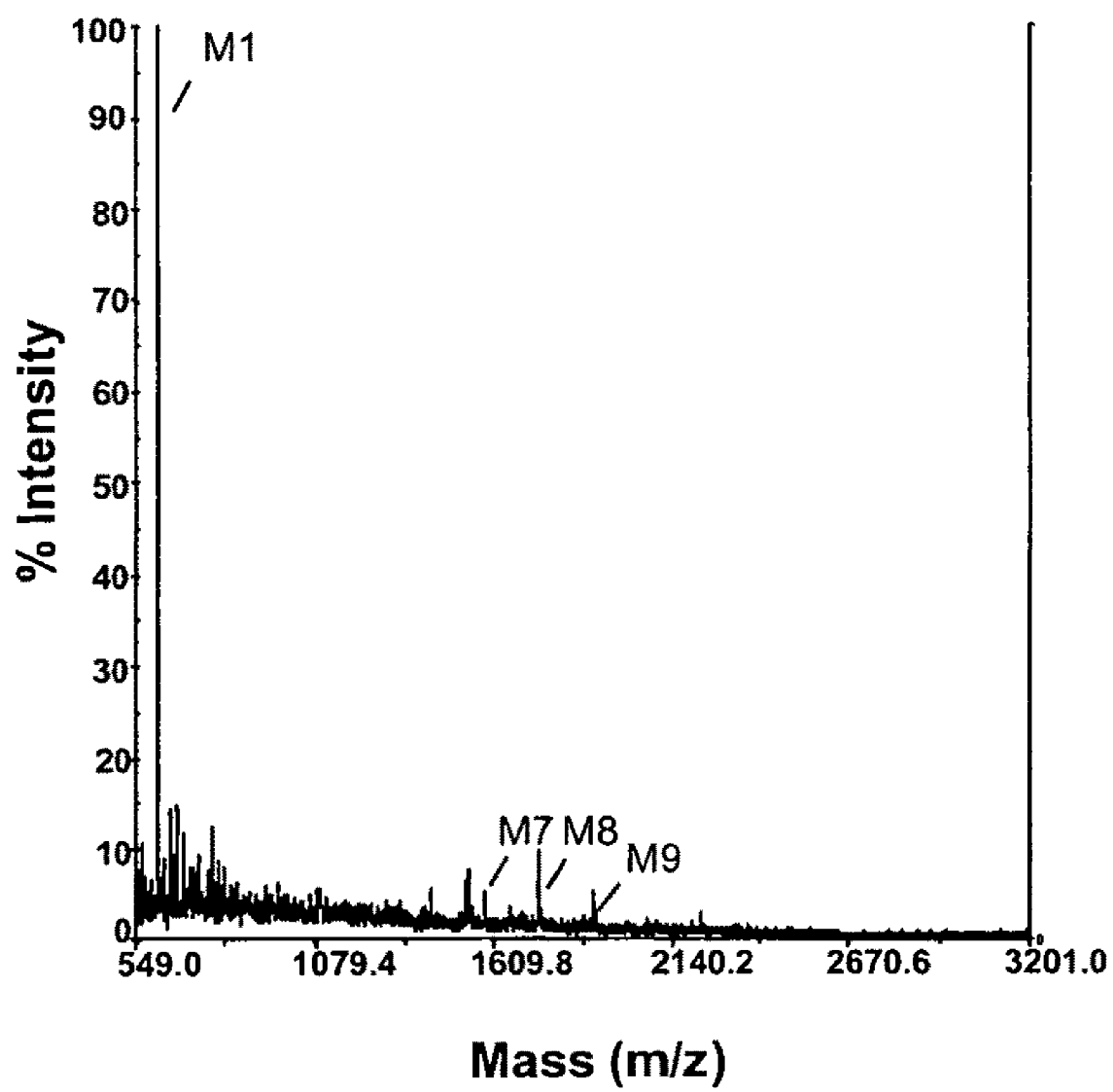
FIG. 3 MALDI-TOF MS spectra of the N-glycans of *P. pastoris* YAS137 after digestion with α-1,2 mannosidase and Jack Bean mannosidase.

*P. pastoris* strain YAS137 (Δoch1, Δpno1, Δmnn4b) (U.S. Pat. No. 7,259,007) was used as a host for the AMR2 gene knockout experiment. YAS137 produces charge free N-glycans without outer chain (FIG. 2A). When digested with α-1,2-mannosidase (FIG. 2B) and Jack Bean (with α-1,2/α-1,3/α-1,6 activity) mannosidases, a significant percentage of N-glycans purified from strain YAS137 can be converted to $Man_5GlcNAc_2$. However, up to 20% of the total N-glycans are recalcitrant to these α-mannosidases (FIG. 3). The amr2 deletion allele (amr2::$Kan^R$) was generated by the PCR overlap method (FIG. 4). Primers PBS1-2-C3 (SEQ ID NO: 1) (5'-TAATAGTGGAGAAA-CTTGCAAAGG-3') paired with PBS2-KO2 (SEQ ID NO: 2) (5'-GTGCTACCTAAAT-CGTATGTGTCGTTGAAGCTTCCCAATGATAGC-3'), and PBS1-2-KO3 (SEQ ID NO: 3) (5'-CTCCCTATAGT-GAGTCGTATTCATATGAT-GGGTGTTTGCTCACTC-3') paired with PBS1-2-KO4 (SEQ ID NO: 4) (5'-CTTGG-TTCAACGCAGCACTTTG-AC-3') were used to amplify the 5' and 3' flanking regions of the AMR2 gene from genomic DNA (genomic DNA was isolated from strain NRRL-Y11430). Primers PR29 (SEQ ID NO: 5) (5'-CACATAC-GATTTAG-GTGACAC-3') paired with PR32 (SEQ ID NO: 6) (5'-AATACGACTCACTATAGG-GAG-3') were used to amplify the Kan (G418) resistance marker from vector pUG6 (Goldstein and McCusker, 1999). Subsequently, primers PBS1-2-C3 and PBS1-2-KO4 were used in a second reaction with all three products from the first round of PCR reactions to generate an overlap product. The resulting fusion PCR product was used to transform strain YAS137. DNA for transformation was prepared by adding sodium acetate to a final concentration of 0.3 M. One hundred percent ice-cold ethanol was then added to a final concentration of 70% to the DNA sample. DNA was pelleted by centrifugation (12000 g×10 min) and washed twice with 70% ice-cold ethanol. The DNA was dried and then resuspended in 50 μl of 10 mM Tris, pH 8.0. YAS137 was prepared by expanding a yeast culture in BMGY (buffered minimal glycerol: 100 mM potassium phosphate, pH 6.0; 1.34% yeast nitrogen base; $4 \times 10^{-5}$% biotin; 1% glycerol) to an O.D. of ~2-6. The yeast were made electrocompetent by washing 3 times in 1M sorbitol and resuspending in ~1-2 mls 1M sorbitol. DNA (1-2 μg) was mixed with 50 μl of competent yeast and incubated on ice for 1 min. Yeast were then electroporated with a BTX Electrocell Manipulator 600 using the following parameters: 1.5 kV, 129 ohms, and 25 μF. One milliliter of YPDS (1% yeast extract, 2% peptone, 2% dextrose, 1M sorbitol) was added to the electroporated cells. Transformed yeast was subsequently plated on selective agar plates. Transformants were selected on YPD medium containing 200 μg/ml of G418 sulfate, GIBCO™. Proper integration of deletion allele amr2::$Kan^R$ was confirmed by PCR. Screening for knockouts was performed by PCR amplification of both the 5' and 3' portions of the knockout construct. PBS1-C5 (SEQ ID NO: 7) (5'-TTTTCCTCA-AGCCTTCAAA-GACAG-3') and PTEF (SEQ ID NO: 8) (5'-AGCTGCGCA-CGTCAAGACTGT-CAA-GG-3') primers were used to screen the 5' portion of the knockout construct while PBS1-2-C2 (SEQ ID NO: 9) (5'-TACCGATACATAC-GTAGCCAACAC-3') and KAN10 (SEQ ID NO: 10) (5'-TCGCTATACTGCTG-TCGATTC-GATAC-3') primers were used to screen the 3' portion of the knockout construct. Observation of a PCR product in both screens is indicative of a successful knockout of the AMR2 gene since primers PTEF and KAN10 anneal at the 5' and 3' ends of the drug resistance marker sequence, respectively; and PBS1-C5 and PBS1-2-C2 are complimentary to sequences in the genome that flank the 5' and 3' regions of DNA used in the knockout construct. The new (Δoch1, Δpno1, Δmnn4b, Δamr2) strain was designated PBP130.

PCR Amplification

An Eppendorf Mastercycler was used for all PCR reactions. PCR reactions contained template DNA, 125 µM dNTPs, 0.2 µM each of forward and reverse primer, Ex Taq polymerase buffer (Takara Bio Inc.), and Ex Taq polymerase (Takara Bio Inc.). The DNA fragments 5' to the predicted AMR2 gene, 3' to the predicted AMR2 gene, and the drug resistance marker were amplified with 30 cycles of 10 sec at 98° C., 10 sec at 52° C. and 2 min at 72° C. with an initial denaturation step of 2 min at 94° C. and a final extension step of 10 min at 72° C. PCR samples were separated by agarose gel electrophoresis and the DNA bands were extracted and purified using a Gel Extraction Kit from Qiagen. All DNA purifications were eluted in 10 mM Tris, pH 8.0.

Searches and Alignments

A BLAST search to obtain sequences from completed and incomplete fungal genomes at NCBI, was carried out, leading to the identification of AMR2 homologs as discussed in the Details of the Invention. The alignment shown in FIG. 5 was constructed using the Megalign program (DNAStar) and ClustalW algorithm.

EXAMPLE 4

Determination of α-Mannosidase Resistant N-glycans in *P. pastoris*

N-linked glycans in YAS137 and PBP130 were analyzed by secreting a His-tagged reporter protein expressed under the control of the methanol inducible AOX1 promoter. The reporter protein, K3, contains a single N-linked glycosylation site. Briefly, a shake flask containing BMGY was inoculated with a fresh culture of YAS-130 and grown to an O.D. of ~20. The culture was centrifuged and the cell pellet washed with BMMY (buffered minimal methanol: same as BMGY except 0.5% methanol instead of 1% glycerol). The cell pellet was resuspended in BMMY to a volume ⅕ of the original BMGY culture and placed in a shaker for 24 h. The secreted protein was harvested by pelleting the biomass by centrifugation and transferring the culture medium to a fresh tube. The His-tagged K3 protein was then purified on a Ni-affinity column and digested with PNGase (Choi et al., 2003).

EXAMPLE 5

Analysis of Man10 and Man11/12

Structural analysis of the glycans recalcitrant to α-mannosidase digestion disclosed at least one β1,2-mannosyl residue linked to a core mannose oligosaccharide. Structure I shows a proposed β-mannosyl residue 13 shown on branch 5, which can be definitively linked to that chain, and is likely to be an integral part of the high-mannose structure. The residues on the following glycan structure (Structure I) was numbered based on the paper by Ziegler et al, (Ziegler, F. D., J. Cavanagh, C. Lubowski, R. B. Trimble, 1999, Glycobiology 9:497-505), with additional numbers (13,14,15) added arbitrarily.

Structure I

```
                9
       ...[Manα(1-2)]Manα(1-6)  6
                              \
                              Manα(1-6)  4
                              /         \
                ...Manα(1-3)  7          \  3          2              1
                            15            Manββ(1-4)GlcNAcβ1-4)GlcNAc
            [Manα]-[Manα(1-6)]  12       /
                                \       /
                                 Manα(1-3)  5
       14      13       11       8   /
  ...[Manα(1-2)]Manβ(1-2)Manαα(1-2)Manα(1-2)
```

Data from three samples were analyzed for the presence of β-mannosyl residues.

Sample 1: "man10"—this was the original sample described as a man9/10 mixture

Sample 2: "man11"—this was a second preparation described as man11/man12 mixture from P4 fractions 63-66 with estimated 50% man11, 15% man12.

Sample 3: "man10_digest"—this was a third preparation wherein the original man11/man12 mixture was treated with a1,2-mannosidase to trim back to man9 or man10.

A fourth sample containing the core man8/man9 mixture was also examined.

Samples were lyophilized from D2O, and redissolved into 200 uL or 500 uL D2O.

NMR data were collected on Varian Inova 600 MHz and 800 MHz spectrometers at 25 C.

Standard experiments from the Varian library (gradient COSY, TOCSY, NOESY, gradient HSQC and HMBC) were used for characterization.

Evidence for β-Mannosyl Residues:

All three samples have NMR signals that are consistent with β-anomers. Three spectral features support this argument: chemical shifts, H1-H2 scalar coupling, and intra-molecular NOE measurements.

Proton Chemical Shifts.

The chemical shift values of the anomeric protons for α-mannosyl residues are typically greater than 5.0 ppm, whereas the β-mannosyl residues are usually less than 5.0 ppm. There are exceptions, such as a-mannosyl residues 3, 4 and 12, so this alone does not prove anomeric configuration.

Analysis showing the anomeric region of proton 1D spectra of the four samples, revealed two peaks 13 and 13t, which correspond to a β-mannosyl residue linked 1-2 to 11, where 13t is a terminal residue, and 13 seems further substituted with an α-mannosyl residue 14. One can compare these spectra to NMR data from high-mannose structures found in Ziegler et al., which show only the core residues 3 and 4, and the residue 12, in the chemical shift region below 5 ppm.

Additional chemical shifts were extracted from the 2D TOCSY data, which shows distinct H1,H2,H3,H4 and H5 signals from residue 13 which correspond closely to data reported in Trinel et al, JBC 1999 and Nitz et al, JBC 2002. The signals from the terminal residue 13t are not as well separated but have similar shifts (see Table 1).

The 2D TOCSY (a proton-proton correlated map) showed crosspeaks belonging to the β-Man 13 residue (data not shown). Chemical shifts of β-mannosyl residues and the literature values are listed in Table 1.

TABLE 1

|  | H1 | H2 | H3 | H4 | H5 |
| --- | --- | --- | --- | --- | --- |
| β-man 13 | 4.90 | 4.35 | 3.75 | 3.64 | 3.40 |
| β-man 13t | 4.86 | 4.27 | 3.67 | 3.47 | 3.40 |
| Trinel et al. | 4.90-5.05 | 4.16-4.41 | 3.63-3.73 | 3.47-3.59 | 3.41 |
| Nitz et al. | 4.95 | 4.42 | 3.62 | 3.56 |  |

Chemical shifts for a-Mannosyl residues have generally the same order, but the values for H2 are typically ~0.1 ppm lower, H3 are ~0.1 ppm higher and H5 are ~0.2 ppm higher.

(Trinel, P.-A., Y. Plancke, P. Gerold, T. Jouault, F. Delplace, R. T. Schwarz, G. Strecker, and D. Poulain, 1999, *J. Biol. Chem.* 274:30520-30526) (Nitze. M, C.-C. Ling, A. Otter, J. E. Cutler, D. R. Bundle, 2002, *J. Biol. Chem.*, 277:3440-3446)

NOE Crosspeaks.

The β-anomeric proton is on the same face of the pyranose ring as the H3 and H5 and about 2.4 Angstroms apart, whereas the α-anomeric proton is on the opposite face, and closer to 4 Ang. from either H3 or H5. Therefore, one expects a strong NOE signal between H1 and H3 and H5 in the β-anomer. This is clearly shown in the NOESY data (not shown), where the spectrum shows the NOE crosspeaks that arise from through space interactions and are highly distance dependent. The horizontal line at 4.895 ppm corresponds to the H1 of the β-man 13 residue (data not shown). The vertical lines confirm the assignment of these peaks to specific resonances, as determined by the TOCSY experiment in the top panel. The strong peaks H3 and H5 are due to intra-residue NOEs between H1 and H3 or H5, confirming the β-anomeric assignment (data not shown).

H1 to H2 Scalar Coupling ('Splitting' of Peaks)

The magnitude of the proton scalar coupling that gives rise to 'splittings' of resonances and multiplet structure is related to the relative orientation of the protons involved. It can thus be an indication of anomeric configuration.

The H1-H2 scalar coupling in α-mannosyl residues is about 1.5 Hz, whereas the β-anomer is <1 Hz. In spectra with very narrow lines you can see the splitting for the α-anomer, whereas the β-anomer is too small and the signals look like singlets. In these data, the linewidth was not optimal, so both sets of peaks look like singlets. However, the pattern and intensity of peaks in the 2D TOCSY (data not shown) is also dependent on the magnitude of the coupling. A region from the TOCSY spectrum shows where the horizontal lines correspond to H1 signals, and the crosspeaks are from other protons in the respective residues. First the peaks in the H2 region that are linked to β-Man residues (3,13,13t) are lower intensity than the α-Man peaks (e.g. 4). The intensity is a rough indication of the efficiency of the signal transfer and therefore the size of the coupling constant.

The α-anomers also show additional crosspeaks from H1 to H3 and sometimes H4—this means that the scalar coupling between H1 and H2 is sufficiently large to allow transfer of the signal beyond H2. The β-anomers, on the other hand, show only H1 to H2 crosspeaks; since the coupling is so small the transfer of signal is very inefficient and doesn't continue to other protons in the ring. The patterns for 13, 13t and 3 are the same, but clearly different from the other mannosyl residues.

Evidence for Linkage Position of β-mannosyl 13(t).

Changes in H1 and H2 Chemical Shifts.

For a known high-mannose structure, it is usually sufficient to compare the H1 and H2 proton chemical shifts with standard literature values to arrive at a structure. In this case, anomalous signals required more effort to establish linkages. However, there were some peaks that could be assigned to the core structure, such as shown for the Man8/9 spectrum. Comparing the Man8/9 and the Man9/10 spectra (data not shown), there are many differences, including the new signals 13 and 13t, which have been described above as β-mannosyl residues.

Comparing the spectra of samples Man9/10 and Man11/12, the terminal α-mannosyl residues similar to 9 have returned. This would suggest the peak labeled 6,12 in the Man9/10 spectrum is likely to be terminal 6, since it is expected to shift upon substitution with another α-mannose. It returns to the original position in the mannosidase digested sample, Man 10-digest. The carbon-proton correlated data (HSQC, HMBC spectra not shown) from the Man11, and Man10-digest samples confirms that this residue is connected in a 1-6 linkage.

The signal labeled 14, is proposed to be an α-mannosyl residue linked to 13, rather than a substituted mannosyl residue 7, as is seen in typical Man9 structures. This is based on the NOE data discussed below. However, to account for the chemical shift of the anomeric proton, it is probably further substituted.

Analysis of NOE Data.

The primary data for determining linkage sites are from NOE spectra, which indicates protons that are close in space. Therefore, in addition to intra-residue NOE crosspeaks, one can also observe inter-residue crosspeaks, which usually indicate the linkage position. In the case of Man(1-2) linkages, one observes crosspeaks between H1 and H2 in the same residue, between H1 and H2 of the glycosidically linked residue, and often between H1 and H1 of the glycosidically linked residue.

Regions from the NOESY and TOCSY spectrum of the man10 sample were analyzed (data not shown). In the top panel, the peaks represent the correlation between H1 and H2 of the identified mannosyl residues. In the middle panel, the signal labeled 11 shows an NOE correlation (box) between H1 and H2 of mannosyl residue 8, consistent with its assignment. If we examine the NOE crosspeaks from the anomeric protons of residues 13 and 13t, there are correlations with H2 of mannosyl residue 11. This links the β-mannosyl residues to the 1-3 branch of the core oligosaccharide. The lower panel shows an additional strong NOE correlation between H1 of 13t and H1 of 11, also consistent with a β(1-2) linkage.

Additional support for this structural fragment comes from the unusual chemical shift of the H2 of mannosyl residue 11; its value is consistent with data from Trimble et al (Trimble, R. B., C. Lubowski, C. Hauer III, R. Stack, L. McNaughton, T. Gemmill, and S. Anand Kumar, 2004, Glycobiology 14:265-274)) showing chemical shifts of 4.26 ppm for α-mannosyl residues 2-substituted by β-man. In addition, proton-carbon correlated data (HSQC and HMBC spectra, not shown) indicate that the carbon chemical shifts of the C2 of mannosyl 11 (as well as 8 and 5, for example) are at high values (~82-84 ppm) characteristic of carbons in glycosidic linkages.

We conclude that at least one β-mannosyl residue can be shown to be linked 1-2 to a core mannose oligosaccharide. There may be multiple linkage sites for the β-mannosyl residues, and they themselves may be substituted.

REFERENCES

Choi, B-K. et al. 2003. Use of combinatorial genetic libraries to humanize N-linked glycosylation in yeast *Pichia pastoris*. *Proc. Natl. Acad. Sci.* 1100; 5022-5027.

Cregg, J. M. et al. 2000. Recombinant protein expression in *Pichia pastoris*. *Mol. Biotechnol.* 16; 23-52.

Cutler, J. E. 2001 N-glycosylation of yeast, with emphasis on *Candida albicans*. *Med. Mycology.* 39; S75-S86.

Han, Y., Kanbe, T., Chemiak, R. and Cutler, J. E. 1997. Biochemical characterization of *Candida albicans* epitopes that can elicit protective and nonprotective antibodies. *Infect. Immun.* 65; 4100-4107.

Joualt, T., Delaunoy, C. Sendid, B., Ajana, R. and Poulain, D. 1997. Differential humoral response against α- and β-linked mannose residues associated with tissue invasion by *Candida albicans*. *Clin. Diagn. Lab. Immunol.* 4; 328-333.

Kobayashi, H., Shibata, N. and Suzuki, S. 1986. Acetolysis of *Pichia pastoris* IFO 0948 Strain Mannan Containing α-1,2 and β1,2 Linkages Using Acetolysis medium of Low Sulfuric Acid Concentration. *Arch. Biochem. Biophys.* 245; 494-508.

Kobayashi, H et al. 1989. Structural study of phosphomannan of yeast-form cells of *Candida albicans* J-1012 strain with special reference to application of mild acetolysis. *Arch. Biochem. Biophys.* 272; 364-375.

Kobayashi, H. et al. 1992. Structural study of a cell wall mannan-protein complex of the pathogenic yeast *Candida glabrata* IFO 0622 strain. *Arch. Biochem. Biophys.* 294; 662-669.

Kobayashi, H. et al. 1994. Structural modification of cell wall mannans of *Candida albicans* serotype A strains grown in yeast extract-Sabouraud liquid medium under acidic conditions. *Infect. Immun.* 62; 968-973.

Rosenfeld, L. and Ballou, C. 1974. Genetic Control of Yeast Mannan Structure. *J. Biol. Chem.* 249; 2319-2321.

Shibata, N., Ichikawa, T., Tojo, M. et al. 1985. Immunochemical study on the mannans of *Candida albicans* NIH A-207, NIH B-792 and J-1012 strains prepared by fractional precipitation with cetyltrimethylammonium bromide. *Arch. Biochem. Biophys.* 243; 338-348.

Shibata, N., Hisamichi, K., Kobayashi, H., and Suzuki, S. 1993a. Complete assignment of 1H and 13C nuclear magnetic resonance chemical shifts of beta-1,2-linked mannooligosaccharides isolated from the phosphomannan of the pathogenic yeast *Candida albicans* NIH B-792 strain. *Arch Biochem Biophys.* 302; 113-117.

Shibata, N., Hisamichi, K., Kobayashi, H., and Suzuki, S. 1993b. Structural study of a cell-wall mannan of *Saccharomyces kluyveri* IFO 1685 strain. Presence of a branched side chain and beta-1,2-linkage. *Eur J. Biochem.* 217; 1-12.

Suzuki, A. et al. 1997. Characterization of b-1,2 Mannosyltransferase in *Candida guilliermondii* and Its Utilization in the Synthesis of Novel Oligosaccharides. *J. Biol. Chem.* 272; 16822-16828.

Takeuchi, Makato. 1997. Trial for Molecular Breeding of Yeast for the Production of Glycoprotein Therapeutics. *Trends in Glycoscience and Glycotechnology.* 9; S29-S35.

Trimble, R. B. et al. 2004. Characterization of N- and O-linked glycosylation of recombinant human bile salt-stimulated lipase secreted by *Pichia pastoris*. *Glycobiology.* 14; 265-274.

What is claimed is:

1. A method for producing glycoprotein compositions in *Pichia pastoris* host cells, said glycoprotein compositions having reduced amounts of α-mannosidase resistant glycans on said glycoproteins, said method comprising modifying the host cell by disrupting or deleting a gene encoding a polypeptide involved in 62-mannosylation of N-glycans, wherein said gene encodes the polypeptide sequence of SEQ ID NO:12, wherein the modified host cell produces the glycoproteins that have reduced amounts of α-mannosidase resistant glycans thereon.

2. The method of claim 1, wherein the α-mannosidase resistant glycans comprise α-mannose, branched high mannose, or α-1,4 mannose residues.

3. The method of claim 1, wherein the host cell further comprises deletion of a functional gene product encoding an alpha-1,6-mannosyltransferase activity.

4. The method of claim 1, wherein the host cell further comprises deletion of a functional gene product encoding mannosylphosphate transferase activity.

5. The method of claim 1, wherein the gene encodes a polypeptide having the amino acid sequence of SEQ ID NO:12 and the method further includes deleting or disrupting at least one gene encoding a polypeptide have an amino acid sequence selected from the group consisting of SEQ ID NO:13, SEQ ID NO:14, and SEQ ID NO:15.

6. The method of claim 1, wherein the gene encodes a polypeptide having the amino acid sequence of SEQ ID NO:12 and the method further includes deleting or disrupting at least two genes, each gene encoding a polypeptide have an amino acid sequence selected from the group consisting of SEQ ID NO:13, SEQ ID NO:14, and SEQ ID NO:15.

7. The method of claim 1, wherein the gene encodes a polypeptide having the amino acid sequence of SEQ ID NO:12 and the method further includes deleting or disrupting the genes encoding polypeptides having the amino acid sequence of SEQ ID NO:13, SEQ ID NO:14, and SEQ ID NO:15.

8. The method of claim 1, wherein the glycoprotein is a therapeutic glycoprotein.

9. The method of claim 1, wherein the glycoprotein is a therapeutic glycoprotein selected from the group consisting of erythropoietin, cytokines interferon-α, interferon-β, interferon-γ, interferon-ω, and granulocyte-CSF, GM-CSF, coagulation factors factor VIII, factor IX, and human protein C, antithrombin III, thrombin, soluble IgE receptor α-chain, IgG, IgG fragments, IgG fusions, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon-like protein 1, and IL-2 receptor agonist.

10. A method for producing a therapeutic glycoprotein that lacks α-mannosidase resistant glycans thereon in *Pichia pastoris*, comprising (a) providing a *Pichia pastoris* host cell in which a gene encoding the β-mannosyltransferase having the amino acid sequence of SEQ ID NO:12 is disrupted or deleted and which includes at least one nucleic acid molecule encoding a therapeutic glycoprotein;

(b) growing the host cell under conditions that produce the therapeutic glycoprotein; and (c) recovering the therapeutic glycoprotein.

11. The method of claim 10, wherein the host cell further comprises deletion of a functional gene product encoding an α1,6-mannosyltransferase activity.

12. The method of claim 10, wherein the host cell further comprises deletion of a functional gene product encoding mannosyiphosphate transferase activity.

13. The method of claim 10, wherein the gene encodes a polypeptide having the amino acid sequence of SEQ ID NO:12 and the host cell further includes a disruption or deletion of at least one gene encoding a polypeptide have an amino acid sequence selected from the group consisting of SEQ ID NO:13, SEQ ID NO:14, and SEQ ID NO:15.

14. The method of claim 10, wherein the gene encodes a polypeptide having the amino acid sequence of SEQ ID NO:12 and the host cell further includes a disruption or deletion of at least two genes, each gene encoding a polypeptide have an amino acid sequence selected from the group consisting of SEQ ID NO:13, SEQ ID NO:14, and SEQ ID NO:15.

15. The method of claim 10, wherein the gene encodes a polypeptide having the amino acid sequence of SEQ ID NO:12 and the host cell further includes a disruption or deletion of genes encoding polypeptides having the amino acid sequence of SEQ ID NO:13, SEQ ID NO:14, and SEQ ID NO:15.

16. The method of claim 10, wherein the therapeutic glycoprotein selected from the group consisting of erythropoietin, cytokines interferon-α, interferon-γ, interferon-γ, interferon-ω, and granulocyte-CSF, GM-CSF, coagulation factors factor VIII, factor IX, and human protein C, antithrombin III, thrombin, soluble IgE receptor α-chain, IgG, IgG fragments, IgG fusions, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fe fusion, glucagon-like protein 1, and IL-2 receptor agonist.

* * * * *

SEQUENCE LISTING

<160> NUMBER OF SEQ ID NOS: 23

<210> SEQ ID NO 1
<211> LENGTH: 24
<212> TYPE: DNA
<213> ORGANISM: Artificial Sequence
<220> FEATURE:
<223> OTHER INFORMATION: degenerate oligonucleotide primer

<400> SEQUENCE: 1
taatagtgga gaaacttgca aagg                                              24

<210> SEQ ID NO 2
<211> LENGTH: 45
<212> TYPE: DNA
<213> ORGANISM: Artificial Sequence
<220> FEATURE:
<223> OTHER INFORMATION: degenerate oligonucleotide primer

<400> SEQUENCE: 2
gtgctaccta aatcgtatgt gtcgttgaag cttcccaatg atagc                       45

<210> SEQ ID NO 3
<211> LENGTH: 45
<212> TYPE: DNA
<213> ORGANISM: Artificial Sequence
<220> FEATURE:
<223> OTHER INFORMATION: degenerate oligonucleotide primer

<400> SEQUENCE: 3

-continued ctccctatag tgagtcgtat tcatatgatg ggtgtttgct cactc        45

<210> SEQ ID NO 4
<211> LENGTH: 24
<212> TYPE: DNA
<213> ORGANISM: Artificial Sequence
<220> FEATURE:
<223> OTHER INFORMATION: degenerate oligonucleotide primer

<400> SEQUENCE: 4
cttggttcaa cgcagcactt tgac        24

<210> SEQ ID NO 5
<211> LENGTH: 21
<212> TYPE: DNA
<213> ORGANISM: Artificial Sequence
<220> FEATURE:
<223> OTHER INFORMATION: degenerate oligonucleotide primer

<400> SEQUENCE: 5
cacatacgat ttaggtgaca c        21

<210> SEQ ID NO 6
<211> LENGTH: 21
<212> TYPE: DNA
<213> ORGANISM: Artificial Sequence
<220> FEATURE:
<223> OTHER INFORMATION: degenerate oligonucleotide primer

<400> SEQUENCE: 6
aatacgactc actataggga g        21

<210> SEQ ID NO 7
<211> LENGTH: 24
<212> TYPE: DNA
<213> ORGANISM: Artificial Sequence
<220> FEATURE:
<223> OTHER INFORMATION: degenerate oligonucleotide primer

<400> SEQUENCE: 7
ttttcctcaa gccttcaaag acag        24

<210> SEQ ID NO 8
<211> LENGTH: 26
<212> TYPE: DNA
<213> ORGANISM: Artificial Sequence
<220> FEATURE:
<223> OTHER INFORMATION: degenerate oligonucleotide primer

<400> SEQUENCE: 8
agctgcgcac gtcaagactg tcaagg        26

<210> SEQ ID NO 9
<211> LENGTH: 24
<212> TYPE: DNA
<213> ORGANISM: Artificial Sequence
<220> FEATURE:
<223> OTHER INFORMATION: degenerate oligonucleotide primer

<400> SEQUENCE: 9
taccgataca tacgtagcca acac        24

<210> SEQ ID NO 10
<211> LENGTH: 26
<212> TYPE: DNA
<213> ORGANISM: Artificial Sequence

```
<220> FEATURE:
<223> OTHER INFORMATION: degenerate oligonucleotide primer

<400> SEQUENCE: 10
tcgctatact gctgtcgatt cgatac                                          26

<210> SEQ ID NO 11
<211> LENGTH: 1935
<212> TYPE: DNA
<213> ORGANISM: Pichia pastoris

<400> SEQUENCE: 11
atgagaacac gactcaactt cctgctgctc tgtattgcca gtgttttgtc tgtgatttgg     60
atcggagtcc tccttacttg gaatgataat aatcttggcg gaatctccct aaacggaggc    120
aaggattctg cctatgatga tctgctatca ttgggaagct tcaacgacat ggaggtcgac    180
tcctatgtca ccaacatcta cgacaatgct ccagtgctag gatgtacgga tttgtcttat    240
catggattgt tgaaagtcac cccaaagcat gacttagctt cgatttggga gttcataaga    300
gctcagattt tggacattga cgtttactcc gccataaaag acttagaaga taaagccttg    360
actgtaaaac aaaaggttga aaaacactgg tttacgtttt atggtagttc agtctttctg    420
cccgaacacg atgtgcatta cctggttaga cgagtcatct tttcggctga aggaaaggcg    480
aactctccag taacatctat catagttgct cagatatatg acaaaaactg aacgagtta    540 aatggccatt tcttggacat cctgaaccca aatactggga aggtccagca caacacgttt    600
ccacaagttc ttcctattgc aaccaatttt gtcaaaggta agaagtttcg tggggcagaa    660
gatcctagag ttgttttgag aaagggccgt tttggacctg atcctttggt gatgttcaac    720
tccctaactc aagataacaa acgtaggaga attttttacca tttctccatt tgaccagttc    780
aaaacagtca tgtacgacat taaagactat gagatgccca ggtatgaaaa gaactgggtc    840 ccattttct aaaagacaa tcaggaggca gttcattttg tttactcttt caaccctctg    900
agagtactca aatgcagtct tgatgacggc tcatgtgata ttgtgtttga ataccgaaa    960 gttgactcca tgtcgtctga gttgcgtggt gccacaccta tgatcaatct tcctcaggca   1020
attccgatgg cgaaggacaa agagatctgg gtttcattcc ccagaacgag aattgcaaat   1080
tgtggttgct ccaggacgac atacagacca atgctgatgc tctttgtcag agaaggttca   1140
aatttctttg ttgaactctt gtccacctct cttgattttg gtctggaggt tttaccgtat   1200
tcaggaaacg gattaccatg cagtgcggac cattccgttt taatcccaaa tagcattgat   1260
aactgggaag tcgtagatag caatggagac gatatcttga cattgtcatt cagtgaggcg   1320
gacaagagta cctctgtgat tcatatcaga gggctgtata actatctatc tgaactggat   1380
ggctatcaag tccagaagc agaggatgaa cataatttcc agcgtatcct gagtgactta   1440
cattttgaca caaaaccacc ggtaaacaat tttataaaag tacaatcatg tgcactagat   1500
gctgccaaag gttattgtaa agaatatggg cttactcgtg gggaggcaga acgaagaagg   1560
agggtcgctg aggagagaaa gaagaaggag aaagaggaag aagaaaaaaa gaaaagaaa   1620 gaaaagaaag aagaagagaa aaagaggatt gaagaggaga agaagaagat tgaagaaaag   1680
gaacgaaagg agaaagagaa agaagaagcg gagagaaaaa agctgcaaga atgaaaaag   1740 aaacttgagg aaatcacaga aaaacttgaa aaaggccaga ggaataaaga gatagatcca   1800
aaagagaagc aaagggaaga agaagaaaga aggagagag tcaggaaaat agcggagaaa   1860
caaaggaagg aggcggaaaa gaaggaggct gaaaaaaagg caaatgacaa aaaggatcta   1920
```
aaaataagac agtag                                                                     1935

<210> SEQ ID NO 12
<211> LENGTH: 644
<212> TYPE: PRT
<213> ORGANISM: Pichia pastoris

<400> SEQUENCE: 12

Met Arg Thr Arg Leu Asn Phe Leu Leu Cys Ile Ala Ser Val Leu
1               5                   10                  15

Ser Val Ile Trp Ile Gly Val Leu Leu Thr Trp Asn Asp Asn Leu
            20                  25                  30

Gly Gly Ile Ser Leu Asn Gly Gly Lys Asp Ser Ala Tyr Asp Asp Leu
        35                  40                  45

Leu Ser Leu Gly Ser Phe Asn Asp Met Glu Val Asp Ser Tyr Val Thr
    50                  55                  60

Asn Ile Tyr Asp Asn Ala Pro Val Leu Gly Cys Thr Asp Leu Ser Tyr
65                  70                  75                  80

His Gly Leu Leu Lys Val Thr Pro Lys His Asp Leu Ala Cys Asp Leu
                85                  90                  95

Glu Phe Ile Arg Ala Gln Ile Leu Asp Ile Asp Val Tyr Ser Ala Ile
            100                 105                 110

Lys Asp Leu Glu Asp Lys Ala Leu Thr Val Lys Gln Lys Val Glu Lys
        115                 120                 125

His Trp Phe Thr Phe Tyr Gly Ser Ser Val Phe Leu Pro Glu His Asp
    130                 135                 140

Val His Tyr Leu Val Arg Arg Val Ile Phe Ser Ala Glu Gly Lys Ala
145                 150                 155                 160

Asn Ser Pro Val Thr Ser Ile Ile Val Ala Gln Ile Tyr Asp Lys Asn
                165                 170                 175

Trp Asn Glu Leu Asn Gly His Phe Leu Asp Ile Leu Asn Pro Asn Thr
            180                 185                 190

Gly Lys Val Gln His Asn Thr Phe Pro Gln Val Leu Pro Ile Ala Thr
        195                 200                 205

Asn Phe Val Lys Gly Lys Lys Phe Arg Gly Ala Glu Asp Pro Arg Val
    210                 215                 220

Val Leu Arg Lys Gly Arg Phe Gly Pro Asp Pro Leu Val Met Phe Asn
225                 230                 235                 240

Ser Leu Thr Gln Asp Asn Lys Arg Arg Ile Phe Thr Ile Ser Pro
                245                 250                 255

Phe Asp Gln Phe Lys Thr Val Met Tyr Asp Ile Lys Asp Tyr Glu Met
            260                 265                 270

Pro Arg Tyr Glu Lys Asn Trp Val Pro Phe Phe Leu Lys Asp Asn Gln
        275                 280                 285

Glu Ala Val His Phe Val Tyr Ser Phe Asn Pro Leu Arg Val Leu Lys
    290                 295                 300

Cys Ser Leu Asp Asp Gly Ser Cys Asp Ile Val Phe Glu Ile Pro Lys
305                 310                 315                 320

Val Asp Ser Met Ser Ser Glu Leu Arg Gly Ala Thr Pro Met Ile Asn
                325                 330                 335

Leu Pro Gln Ala Ile Pro Met Ala Lys Asp Lys Glu Ile Trp Val Ser
            340                 345                 350

Phe Pro Arg Thr Arg Ile Ala Asn Cys Gly Cys Ser Arg Thr Thr Tyr
        355                 360                 365

```
Arg Pro Met Leu Met Leu Phe Val Arg Glu Gly Ser Asn Phe Phe Val
    370                 375                 380
Glu Leu Leu Ser Thr Ser Leu Asp Phe Gly Leu Glu Val Leu Pro Tyr
385                 390                 395                 400
Ser Gly Asn Gly Leu Pro Cys Ser Ala Asp His Ser Val Leu Ile Pro
                405                 410                 415
Asn Ser Ile Asp Asn Trp Glu Val Val Asp Ser Asn Gly Asp Asp Ile
            420                 425                 430
Leu Thr Leu Ser Phe Ser Glu Ala Asp Lys Ser Thr Ser Val Ile His
        435                 440                 445
Ile Arg Gly Leu Tyr Asn Tyr Leu Ser Glu Leu Asp Gly Tyr Gln Gly
    450                 455                 460
Pro Glu Ala Glu Asp Glu His Asn Phe Gln Arg Ile Leu Ser Asp Leu
465                 470                 475                 480
His Phe Asp Asn Lys Thr Thr Val Asn Asn Phe Ile Lys Val Gln Ser
                485                 490                 495
Cys Ala Leu Asp Ala Ala Lys Gly Tyr Cys Lys Glu Tyr Gly Leu Thr
            500                 505                 510
Arg Gly Glu Ala Glu Arg Arg Arg Val Ala Glu Glu Arg Lys Lys
    515                 520                 525
Lys Glu Lys Glu Glu Glu Glu Lys Lys Lys Lys Glu Lys Glu Glu
530                 535                 540
Glu Glu Lys Lys Arg Ile Glu Glu Lys Lys Ile Glu Glu Lys
545                 550                 555                 560
Glu Arg Lys Glu Lys Glu Lys Glu Ala Glu Arg Lys Lys Leu Gln
            565                 570                 575
Glu Met Lys Lys Lys Leu Glu Glu Ile Thr Glu Lys Leu Glu Lys Gly
            580                 585                 590
Gln Arg Asn Lys Glu Ile Asp Pro Lys Glu Lys Gln Arg Glu Glu Glu
            595                 600                 605
Glu Arg Lys Glu Arg Val Arg Lys Ile Ala Glu Lys Gln Arg Lys Glu
        610                 615                 620
Ala Glu Lys Lys Glu Ala Glu Lys Lys Ala Asn Asp Lys Lys Asp Leu
625                 630                 635                 640
Lys Ile Arg Gln

<210> SEQ ID NO 13
<211> LENGTH: 652
<212> TYPE: PRT
<213> ORGANISM: Pichia pastoris

<400> SEQUENCE: 13

Met Val Asp Leu Phe Gln Trp Leu Lys Phe Tyr Ser Met Arg Arg Leu
1               5                   10                  15
Gly Gln Val Ala Ile Thr Leu Val Leu Leu Asn Leu Phe Val Phe Leu
            20                  25                  30
Gly Tyr Lys Phe Thr Pro Ser Thr Val Ile Gly Ser Pro Ser Trp Glu
        35                  40                  45
Pro Ala Val Val Pro Thr Val Phe Asn Glu Ser Tyr Leu Asp Ser Leu
    50                  55                  60
Gln Phe Thr Asp Ile Asn Val Asp Ser Phe Leu Ser Asp Thr Asn Gly
65                  70                  75                  80
Arg Ile Ser Val Thr Cys Asp Ser Leu Ala Tyr Lys Gly Leu Val Lys
                85                  90                  95
```

-continued

```
Thr Ser Lys Lys Lys Glu Leu Asp Cys Asp Met Ala Tyr Ile Arg Arg
            100                 105                 110

Lys Ile Phe Ser Ser Glu Glu Tyr Gly Val Leu Ala Asp Leu Glu Ala
            115                 120                 125

Gln Asp Ile Thr Glu Glu Gln Arg Ile Lys Lys His Trp Phe Thr Phe
            130                 135                 140

Tyr Gly Ser Ser Val Tyr Leu Pro Glu His Glu Val His Tyr Leu Val
145                 150                 155                 160

Arg Arg Val Leu Phe Ser Lys Val Gly Arg Ala Asp Thr Pro Val Ile
                165                 170                 175

Ser Leu Leu Val Ala Gln Leu Tyr Asp Lys Asp Trp Asn Glu Leu Thr
                180                 185                 190

Pro His Thr Leu Glu Ile Val Asn Pro Ala Thr Gly Asn Val Thr Pro
                195                 200                 205

Gln Thr Phe Pro Gln Leu Ile His Val Pro Ile Glu Trp Ser Val Asp
            210                 215                 220

Asp Lys Trp Lys Gly Thr Glu Asp Pro Arg Val Phe Leu Lys Pro Ser
225                 230                 235                 240

Lys Thr Gly Val Ser Glu Pro Ile Val Leu Phe Asn Leu Gln Ser Ser
                245                 250                 255

Leu Cys Asp Gly Lys Arg Gly Met Phe Val Thr Ser Pro Phe Arg Ser
                260                 265                 270

Asp Lys Val Asn Leu Leu Asp Ile Glu Asp Lys Glu Arg Pro Asn Ser
            275                 280                 285

Glu Lys Asn Trp Ser Pro Phe Phe Leu Asp Asp Val Glu Val Ser Lys
            290                 295                 300

Tyr Ser Thr Gly Tyr Val His Phe Val Tyr Ser Phe Asn Pro Leu Lys
305                 310                 315                 320

Val Ile Lys Cys Ser Leu Asp Thr Gly Ala Cys Arg Met Ile Tyr Glu
                325                 330                 335

Ser Pro Glu Glu Gly Arg Phe Gly Ser Glu Leu Arg Gly Ala Thr Pro
            340                 345                 350

Met Val Lys Leu Pro Val His Leu Ser Leu Pro Lys Gly Lys Glu Val
            355                 360                 365

Trp Val Ala Phe Pro Arg Thr Arg Leu Arg Asp Cys Gly Cys Ser Arg
            370                 375                 380

Thr Thr Tyr Arg Pro Val Leu Thr Leu Phe Val Lys Glu Gly Asn Lys
385                 390                 395                 400

Phe Tyr Thr Glu Leu Ile Ser Ser Ile Asp Phe His Ile Asp Val
                405                 410                 415

Leu Ser Tyr Asp Ala Lys Gly Glu Ser Cys Ser Gly Ser Ile Ser Val
                420                 425                 430

Leu Ile Pro Asn Gly Ile Asp Ser Trp Asp Val Ser Lys Lys Gln Gly
            435                 440                 445

Gly Lys Ser Asp Ile Leu Thr Leu Thr Leu Ser Glu Ala Asp Arg Asn
            450                 455                 460

Thr Val Val Val His Val Lys Gly Leu Leu Asp Tyr Leu Leu Val Leu
465                 470                 475                 480

Asn Gly Glu Gly Pro Ile His Asp Ser His Ser Phe Lys Asn Val Leu
                485                 490                 495

Ser Thr Asn His Phe Lys Ser Asp Thr Thr Leu Leu Asn Ser Val Lys
                500                 505                 510

Ala Ala Glu Cys Ala Ile Phe Ser Ser Arg Asp Tyr Cys Lys Lys Tyr
```

-continued

```
            515                 520                 525
Gly Glu Thr Arg Gly Glu Pro Ala Arg Tyr Ala Lys Gln Met Glu Asn
            530                 535                 540

Glu Arg Lys Glu Lys Glu Lys Glu Lys Glu Ala Lys Glu Lys Leu
545                 550                 555                 560

Glu Ala Glu Lys Ala Glu Met Glu Ala Val Arg Lys Ala Gln Glu
                565                 570                 575

Ala Ile Ala Gln Lys Glu Arg Glu Lys Glu Ala Glu Gln Glu Lys
                580                 585                 590

Lys Ala Gln Gln Glu Ala Lys Lys Glu Ala Glu Lys Ala Ala
                595                 600                 605

Lys Glu Lys Glu Ala Lys Glu Asn Glu Ala Lys Lys Ile Ile Val
            610                 615                 620

Glu Lys Leu Ala Lys Glu Gln Glu Ala Glu Lys Leu Glu Ala Lys
625                 630                 635                 640

Lys Lys Leu Tyr Gln Leu Gln Glu Glu Arg Ser
                645                 650

<210> SEQ ID NO 14
<211> LENGTH: 594
<212> TYPE: PRT
<213> ORGANISM: Pichia pastoris

<400> SEQUENCE: 14

Met Arg Ile Arg Ser Asn Val Leu Leu Ser Thr Ala Gly Ala Leu
1               5                   10                  15

Ala Leu Val Trp Phe Ala Val Phe Ser Trp Asp Asp Lys Ser Ile
                20                  25                  30

Phe Gly Ile Pro Thr Pro Gly His Ala Val Ala Ser Ala Tyr Asp Ser
            35                  40                  45

Ser Val Thr Leu Gly Thr Phe Asn Asp Met Glu Val Asp Ser Tyr Val
        50                  55                  60

Thr Asn Ile Tyr Asp Asn Ala Pro Val Leu Gly Cys Tyr Asp Leu Ser
65                  70                  75                  80

Tyr His Gly Leu Leu Lys Val Ser Pro Lys His Glu Ile Leu Cys Asp
                85                  90                  95

Met Lys Phe Ile Arg Ala Arg Val Leu Glu Thr Glu Ala Tyr Ala Ala
                100                 105                 110

Leu Lys Asp Leu Glu His Lys Lys Leu Thr Glu Glu Lys Ile Glu
            115                 120                 125

Lys His Trp Phe Thr Phe Tyr Gly Ser Ser Val Phe Leu Pro Asp His
    130                 135                 140

Asp Val His Tyr Leu Val Arg Arg Val Phe Ser Gly Glu Gly Lys
145                 150                 155                 160

Ala Asn Arg Pro Ile Thr Ser Ile Leu Val Ala Gln Ile Tyr Asp Lys
                165                 170                 175

Asn Trp Asn Glu Leu Asn Gly His Phe Leu Asn Val Leu Asn Pro Asn
            180                 185                 190

Thr Gly Lys Leu Gln His His Ala Phe Pro Gln Val Leu Pro Ile Ala
        195                 200                 205

Val Asn Trp Asp Arg Asn Ser Lys Tyr Arg Gly Gln Glu Asp Pro Arg
    210                 215                 220

Val Val Leu Arg Arg Gly Arg Phe Gly Pro Asp Pro Leu Val Met Phe
225                 230                 235                 240
```

```
Asn Thr Leu Thr Gln Asn Asn Lys Leu Arg Arg Leu Phe Thr Ile Ser
                245                 250                 255

Pro Phe Asp Gln Tyr Lys Thr Val Met Tyr Arg Thr Asn Ala Phe Lys
            260                 265                 270

Met Gln Thr Thr Glu Lys Asn Trp Val Pro Phe Phe Leu Lys Asp Asp
        275                 280                 285

Gln Glu Ser Val His Phe Val Tyr Ser Phe Asn Pro Leu Arg Val Leu
    290                 295                 300

Asn Cys Ser Leu Asp Asn Gly Ala Cys Asp Val Leu Phe Glu Leu Pro
305                 310                 315                 320

His Asp Phe Gly Met Ser Ser Glu Leu Arg Gly Ala Thr Pro Met Leu
                325                 330                 335

Asn Leu Pro Gln Ala Ile Pro Met Ala Asp Asp Lys Glu Ile Trp Val
            340                 345                 350

Ser Phe Pro Arg Thr Arg Ile Ser Asp Cys Gly Cys Ser Glu Thr Met
        355                 360                 365

Tyr Arg Pro Met Leu Met Leu Phe Val Arg Glu Gly Thr Asn Phe Phe
    370                 375                 380

Ala Glu Leu Leu Ser Ser Ser Ile Asp Phe Gly Leu Glu Val Ile Pro
385                 390                 395                 400

Tyr Thr Gly Asp Gly Leu Pro Cys Ser Ser Gly Gln Ser Val Leu Ile
                405                 410                 415

Pro Asn Ser Ile Asp Asn Trp Glu Val Thr Gly Ser Asn Gly Glu Asp
            420                 425                 430

Ile Leu Ser Leu Thr Phe Ser Glu Ala Asp Lys Ser Thr Ser Val Val
        435                 440                 445

His Ile Arg Gly Leu Tyr Lys Tyr Leu Ser Glu Leu Asp Gly Tyr Gly
    450                 455                 460

Gly Pro Glu Ala Glu Asp Glu His Asn Phe Gln Arg Ile Leu Ser Asp
465                 470                 475                 480

Leu His Phe Asp Gly Lys Lys Thr Ile Glu Asn Phe Lys Lys Val Gln
                485                 490                 495

Ser Cys Ala Leu Asp Ala Ala Lys Ala Tyr Cys Lys Glu Tyr Gly Val
            500                 505                 510

Thr Arg Gly Glu Glu Asp Arg Leu Lys Asn Lys Glu Lys Glu Arg Lys
        515                 520                 525

Ile Glu Glu Lys Arg Lys Lys Glu Glu Arg Lys Lys Lys Glu Glu
    530                 535                 540

Glu Lys Lys Lys Lys Glu Glu Glu Lys Lys Lys Lys Lys Glu Glu Glu
545                 550                 555                 560

Glu Glu Glu Glu Lys Arg Leu Lys Glu Leu Lys Lys Leu Lys Glu
                565                 570                 575

Leu Gln Glu Glu Leu Glu Lys Gln Lys Asp Glu Val Lys Asp Thr Lys
            580                 585                 590

Ala Lys

<210> SEQ ID NO 15
<211> LENGTH: 503
<212> TYPE: PRT
<213> ORGANISM: Pichia pastoris

<400> SEQUENCE: 15

Met Lys Leu Asp Thr Gln Gln Ile Ser His Leu Leu Ser Arg Gln Met
1               5                   10                  15
```

-continued

```
Tyr His Leu Ala Pro Arg Lys Lys Leu Leu Ile Trp Gly Gly Ser Leu
         20                  25                  30

Gly Phe Val Leu Leu Leu Ile Val Ala Ser Ser His Gln Arg Ile
         35                  40                  45

Arg Ser Thr Ile Leu His Arg Thr Pro Ile Ser Thr Leu Pro Val Ile
 50                  55                  60

Ser Gln Glu Val Ile Thr Ala Asp Tyr His Pro Thr Leu Leu Thr Gly
65                   70                  75                  80

Phe Ile Pro Thr Asp Ser Asp Asp Ser Asp Cys Ala Asp Phe Ser Pro
                 85                  90                  95

Ser Gly Val Ile Tyr Ser Thr Asp Lys Leu Val Leu His Asp Ser Leu
                100                 105                 110

Lys Asp Ile Arg Asp Ser Leu Leu Lys Thr Gln Tyr Lys Asp Leu Val
            115                 120                 125

Thr Leu Glu Asp Glu Glu Lys Met Asn Ile Asp Asp Ile Leu Lys Arg
        130                 135                 140

Trp Tyr Thr Leu Ser Gly Ser Ser Val Trp Ile Pro Gly Met Lys Ala
145                 150                 155                 160

His Leu Val Val Ser Arg Val Met Tyr Leu Gly Thr Asn Gly Arg Ser
                165                 170                 175

Asp Pro Leu Val Ser Phe Val Arg Val Gln Leu Phe Asp Pro Asp Phe
                180                 185                 190

Asn Glu Leu Lys Asp Ile Ala Leu Lys Phe Ser Asp Lys Pro Asp Gly
            195                 200                 205

Thr Val Ile Phe Pro Tyr Ile Leu Pro Val Asp Ile Pro Arg Glu Gly
        210                 215                 220

Ser Arg Trp Leu Gly Pro Glu Asp Ala Lys Ile Ala Val Asn Pro Glu
225                 230                 235                 240

Thr Pro Asp Asp Pro Ile Val Ile Phe Asn Met Gln Asn Ser Val Asn
                245                 250                 255

Arg Ala Met Tyr Gly Phe Tyr Pro Phe Arg Pro Glu Asn Lys Gln Val
                260                 265                 270

Leu Phe Ser Ile Lys Asp Glu Glu Pro Arg Lys Lys Glu Lys Asn Trp
            275                 280                 285

Thr Pro Phe Phe Val Pro Gly Ser Pro Thr Thr Val Asn Phe Val Tyr
        290                 295                 300

Asp Leu Gln Lys Leu Thr Ile Leu Lys Cys Ser Ile Ile Thr Gly Ile
305                 310                 315                 320

Cys Glu Lys Glu Phe Val Ser Gly Asp Gly Gln Asn His Gly Ile
                325                 330                 335

Gly Ile Phe Arg Gly Gly Ser Asn Leu Val Pro Phe Pro Thr Ser Phe
            340                 345                 350

Thr Asp Lys Asp Val Trp Val Gly Phe Pro Lys Thr His Met Glu Ser
        355                 360                 365

Cys Gly Cys Ser Ser His Ile Tyr Arg Pro Tyr Leu Met Val Leu Val
370                 375                 380

Arg Lys Gly Asp Phe Tyr Tyr Lys Ala Phe Val Ser Thr Pro Leu Asp
385                 390                 395                 400

Phe Gly Ile Asp Val Arg Ser Trp Glu Ser Ala Glu Ser Thr Ser Cys
                405                 410                 415

Gln Thr Ala Lys Asn Val Leu Ala Val Asn Ser Ile Ser Asn Trp Asp
            420                 425                 430

Leu Leu Asp Asp Gly Leu Asp Lys Asp Tyr Met Thr Ile Thr Leu Ser
```

```
              435                 440                 445
Glu Ala Asp Val Val Asn Ser Val Leu Arg Val Arg Gly Ile Ala Lys
    450                 455                 460

Phe Val Asp Asn Leu Thr Met Asp Asp Gly Ser Thr Thr Leu Ser Thr
465                 470                 475                 480

Ser Asn Lys Ile Asp Glu Cys Ala Thr Thr Gly Ser Lys Gln Tyr Cys
                485                 490                 495

Gln Arg Tyr Gly Glu Leu His
                500

<210> SEQ ID NO 16
<211> LENGTH: 778
<212> TYPE: PRT
<213> ORGANISM: candida albicans

<400> SEQUENCE: 16

Met Thr Lys Ser Tyr Met Pro Leu Phe Arg Ser Pro Arg Gln Phe Lys
1               5                   10                  15

Lys Ile Tyr Phe Ile Leu Ile Pro Leu Ile Leu Ala Val Ile Ile Leu
                20                  25                  30

His Val Phe Phe Asp Gly Phe Asn Lys Ile Ser Glu Tyr Ser Pro Thr
            35                  40                  45

Phe Ile Ser Asn Arg Ile Leu Asn His Gln Asp Gln Gln Gln Lys Ser
    50                  55                  60

Glu Lys Ser Ser Asp Val Ile Ser Ser Tyr Phe Pro Ser Leu Ala Ile
65                  70                  75                  80

Tyr Pro Lys Asn Phe Asp Asn Arg Val Glu Phe Val Asn Glu Pro Lys
                85                  90                  95

Asn Ser Lys Trp Ile Gln Tyr Phe Gly Asp Ser Lys Thr Val Leu Ser
                100                 105                 110

Asn Tyr Ile Thr Asn Gln Thr Tyr Thr Asn His Ser Ile Gly Leu Tyr
            115                 120                 125

Ser Ser Ser Thr Val Lys Leu Pro Ala Ser Ser Cys Lys Asp Ile Leu
    130                 135                 140

Tyr Glu Arg Ser Phe Glu Ile Thr Lys Tyr Arg Thr Leu His Asp Asp
145                 150                 155                 160

Leu Tyr Lys Leu Ala Thr Thr Leu Ser Tyr Gln Leu Glu Asn Asp Pro
                165                 170                 175

Ala Phe Gln Asp Leu Ser Pro Phe Phe Asn Asp Arg Leu Pro His Ile
            180                 185                 190

Ile Met Arg Gly Glu Leu His Lys His Ile Tyr Lys Phe Ala Gly Thr
    195                 200                 205

Ser Val Trp Leu Glu Gln His Gly Val His Leu Met Leu Ser Arg Val
210                 215                 220

Ile Tyr Ser Gln Gln Gly Lys Lys Asn Asp Pro Gln Leu Ser Leu Leu
225                 230                 235                 240

Tyr Ala Gln Val Tyr Asp Glu Asn Trp Asn Glu Leu Asn Asp Ile Glu
                245                 250                 255

Leu Ile Val Pro Val Ile Asn Pro Asn Gly Glu Arg Val Tyr Asp Ser
            260                 265                 270

Val Lys Tyr Pro Gln Phe Val Ala Ile Pro Phe Tyr His Asn Ser Glu
    275                 280                 285

Tyr Ile Lys Ser Arg Trp Tyr Gly Pro Glu Asp Thr Arg Leu Ile Leu
    290                 295                 300
```

```
Thr Lys Asn Lys Phe Gly Asp Asp Glu Pro Val Ile Ile Phe Asn Ser
305                 310                 315                 320

Tyr His Arg Gln Ile Lys Asp Met Ser Thr Glu Asp Asn Asn Val
            325                 330                 335

His Thr Lys Phe Glu Phe Tyr Arg Ser Met Phe Val Gly Trp Leu Phe
                340                 345                 350

Gln Tyr Gln Leu Gly Lys Leu Asn Thr Asp Gly Ile Gln Asp Ser Lys
            355                 360                 365

Phe Asn Asn Val Thr Phe Asn Lys Val Lys Glu Leu Arg Ile Glu Gly
    370                 375                 380

Lys Glu Arg Thr Ser Ile Glu Lys Asn Trp Thr Pro Phe Ile Asp Pro
385                 390                 395                 400

Asp Glu Arg Asn Gln Ile Ser Tyr Tyr Gly Asn His Asn Leu Gly Asp
                405                 410                 415

Asn Tyr Val Tyr Ile Val Tyr Gln Trp Asn His Leu Lys Ile Leu Lys
            420                 425                 430

Cys Glu Leu Asp Asn Phe Ile Asp Ser Ser His Ser Thr Cys Thr Met
            435                 440                 445

Phe Phe Lys Asp Val Glu Thr Thr Gln Glu Val Gly Pro Val Arg Gly
    450                 455                 460

Gly Thr Glu Leu Trp Pro Ile Lys Ile Asp Asn Asn Asn Asn Asn Asn
465                 470                 475                 480

Asn Leu Asn Glu Asp Asp Leu Ser Thr Lys Gln Glu Pro Gln Gln Gln
            485                 490                 495

Arg Gln Leu Trp Ile Gly Phe Leu Arg Ala His Val Lys Asp Cys Gly
            500                 505                 510

Cys Gly Gly Ser Met Tyr Arg Pro Asn Phe Leu Ile Leu Glu Lys Leu
            515                 520                 525

Asn Ser Lys Phe Lys Leu Thr Tyr Leu Ser Gly Ser Ile Asn Phe Asn
    530                 535                 540

Val Ser Val Tyr Gly Trp Ala Asn Tyr Asp Val Val Cys Ala Gly His
545                 550                 555                 560

Glu Ala Asn Ala Leu Ile Pro Asn Gly Ile Ser Met Phe Asp Gln Asp
                565                 570                 575

Asp Asp Tyr Leu Thr Leu Ser Met Ser Val Ala Asp Gln Asp Asn Thr
            580                 585                 590

Leu Val His Ile His Gly Val Lys Lys Leu Ile Tyr Ser Leu Asp His
            595                 600                 605

Asp Trp Asn Gly Ile Leu Lys Glu Asn Lys Gln Ile Glu Cys Val Val
            610                 615                 620

Asn Asn Ala Asn Asp Phe Cys Lys Ala Tyr Ala Asp Glu His Tyr Lys
625                 630                 635                 640

Leu Gly Asp Ser Glu Ala Ala Ile Lys Glu Val Lys Gln Lys Ala Lys
                645                 650                 655

Glu Glu Ala Glu Lys Ala Lys Ala Glu Lys Glu Lys Ala Glu Lys Glu
            660                 665                 670

Lys Ala Glu Lys Glu Lys Ala Glu Lys Glu Lys Ala Glu Lys Glu Lys
            675                 680                 685

Glu Glu Lys Glu Lys Glu Glu Lys Glu Lys Glu Lys Ala Glu Lys
            690                 695                 700

Glu Lys Glu Glu Lys Glu Lys Ala Glu Lys Glu Leu Ala Glu Lys Glu
705                 710                 715                 720

Leu Ala Glu Gln Lys Asp Glu Asp Ala Lys Asp Glu Asp Lys Asn Glu
```

```
                        725                 730                 735
Asp Glu Asp Asp Lys Glu Lys Asn Asp Glu Ser Gly Leu Thr Glu Lys
                740                 745                 750
Ser Glu Val Glu Glu Asn Gly Glu Asn Thr Ser Glu Gly Ser Glu Gly
                755                 760                 765
Glu Glu Glu Asp Asp Asp Ile Glu Val
            770                 775

<210> SEQ ID NO 17
<211> LENGTH: 694
<212> TYPE: PRT
<213> ORGANISM: Candida albicans

<400> SEQUENCE: 17

Met Lys Phe Pro Lys Leu Arg Lys Arg Thr Val Tyr Trp Ala Val Leu
1               5                   10                  15
Thr Val Phe Ala Leu Phe Thr Ile His Phe Val Phe Gln Tyr Lys Glu
                20                  25                  30
His Asn Ser His Arg Val Gln Pro Ile Val Leu Ile Pro Lys Ala Phe
            35                  40                  45
Pro Ser Leu Ile Leu Asn Ser Phe Asp Thr Gln Asn Glu Glu Leu Val
        50                  55                  60
Pro Ile Lys Leu Leu Lys Asn Cys Gln Ile Ile Arg Ser Tyr His Thr
65                  70                  75                  80
Gly Tyr Glu Glu Asn Thr Lys Leu Leu Gly Gln Glu Pro Gln Ser Asn
                85                  90                  95
Phe His Lys Phe Asn Phe Thr Val Phe Ser Ser Met Lys Pro Ile Gly
            100                 105                 110
Leu Asp Leu Lys Gln Cys Gln Leu Ser Ser Ser Ser Gln Val Glu
        115                 120                 125
Val Asn Asp Ala Val Asn Met Asp Ala Ser Leu His Asp Ile Leu Gly
    130                 135                 140
Lys Leu Leu Gln Asp Ile Arg His Gly Lys Leu Glu Tyr Leu Gln Glu
145                 150                 155                 160
Ile Ala Pro Phe Phe Leu Pro Glu Leu Gln Leu Gln Leu Asn Leu Asn
                165                 170                 175
Ile Val Asp Arg Phe Trp Tyr Arg Phe Ser Gly Ser Ser Ile Trp Leu
            180                 185                 190
Asp Gln Tyr Asn Met Tyr Phe Met Ile Ser Arg Ile Ala Tyr Ser Pro
        195                 200                 205
His Gly Val Lys Asn Gln Pro Val Val Ser Leu Thr Tyr Gly Gln Leu
    210                 215                 220
Phe Asp Arg Asn Trp Asn Glu Val Lys Asn Ile Asn Leu Leu Val Pro
225                 230                 235                 240
Ser Asn Asp Pro Ser Lys Asn Gly Gly His Asp Ser Phe Arg Ile Ile
                245                 250                 255
Ser Phe Pro Tyr Phe Leu Pro Ile Pro Phe Trp His Asp Ile Asp Asn
            260                 265                 270
Thr Asp Gly Asn Tyr Phe Gly Pro Glu Asp Pro Arg Leu Ile Leu Val
        275                 280                 285
Arg Asn Lys Gln Gly Tyr Glu Glu Pro Leu Leu Ile Phe Asn Ser Tyr
    290                 295                 300
His Arg Lys Phe Val His Tyr Asp Asp Asp Glu Asp Ser Ile Met Gly
305                 310                 315                 320
```

```
Gln Thr Val Lys Phe Gln Arg Ser Met Phe Met Cys Trp Pro Trp Gln
                325                 330                 335

Tyr Gln Met Gly Lys Ser Asn Val Glu Gly Thr Ser Asn Pro Glu Tyr
                340                 345                 350

Asp Asn Lys Val Tyr Asn Arg Val Ile Glu Leu Lys Val Lys Leu Leu
                355                 360                 365

Ala Asp Met Lys Ser Gln Lys Asn Trp Thr Pro Phe Ile Ser Glu Asp
            370                 375                 380

Ser Thr Asn Lys Phe Asp Ser Tyr Ile Tyr Phe Val Tyr Arg Trp Ala
385                 390                 395                 400

Asn Leu Asp Val Leu Lys Cys Ser Leu Leu Gly Asp Val Ala Gly Asp
                405                 410                 415

Cys Val Phe Asp Tyr Arg Leu Asp Glu Thr Leu Val Pro Gln Asn Lys
                420                 425                 430

Val Gly Pro Leu Arg Gly Gly Thr Gln Leu Val Asn Leu Arg Gln Val
                435                 440                 445

Ile Pro Arg Ser Val Tyr His Arg Leu Leu Pro Ser His Arg Glu Ile
            450                 455                 460

Phe Ile Gly Phe Ala Arg Thr His Leu Asp Asn Cys Gly Cys Gly Lys
465                 470                 475                 480

Val Met Tyr Arg Pro Asn Leu Val Ile Leu Val Lys Asp Ala Ala Asp
                485                 490                 495

Lys Thr Tyr Tyr Lys Ile Ser His Ile Ser Ser Ser Leu Ser Phe Asp
                500                 505                 510

Val Pro Ile Ile Gly Trp Asn Val Tyr Lys Pro Asp Asp Leu Cys Phe
            515                 520                 525

Asp Ser Asn Val Leu Ile Pro Tyr Ser Val Ser Asn Trp Asn Ile Thr
530                 535                 540

Ser Leu Glu Leu Asp Ile Glu Gly Gly Arg Trp Val Ser Asn Asp Gln
545                 550                 555                 560

Leu Thr Leu Thr Leu Ser Ile Ser Asp Ser Thr Val His Arg Leu Asp
                565                 570                 575

Ile Arg Gly Leu Phe Gln Ser Ile Leu Asp Leu Ala Asp Arg Ser Leu
                580                 585                 590

Phe Ile Pro Val Asp Arg Glu Thr Arg Val Ile Asp Glu Phe Gln Asn
            595                 600                 605

Gly Leu Gln Asn Pro Gly Ser Asn Pro Leu Asn Gln Asp Val Asn Ser
        610                 615                 620

Leu Gly Val Asn Asn Asp Asn Ile Val Cys Ala Leu Asp Ala Ser Val
625                 630                 635                 640

Glu Phe Cys Phe Glu Tyr Gly Ala Lys Phe Ser Ile Pro Lys Gln Glu
                645                 650                 655

Glu Phe Tyr Glu Val Glu Gln Gln Glu Phe Asn Glu Glu Leu Ile Asp
                660                 665                 670

Pro Lys Lys His Gln Tyr Phe Lys Ile Leu Gly Lys Tyr Leu Tyr Asp
            675                 680                 685

His Ala Ser Val Asn Ser
        690

<210> SEQ ID NO 18
<211> LENGTH: 654
<212> TYPE: PRT
<213> ORGANISM: Candida albicans

<400> SEQUENCE: 18
```

```
Met Leu Ala Trp Leu Arg His Arg Ile Arg Ser Tyr Asn Thr Ser Thr
1               5                   10                  15

Tyr Ser Ser Ile Leu Pro Ser Ala Ser Phe Gly Lys Val Tyr Lys Ile
            20                  25                  30

Gly Thr Lys Leu Asn Phe Thr Leu Ala Leu Cys Leu Leu Leu Ala
        35                  40                  45

Cys Ser Val Phe Phe Asn Tyr Phe Tyr Leu Ala Asp Asn Asn Gly Leu
50                      55                  60

Asp Ile Asp Thr Lys Gly Glu Glu Glu Asn Val Phe Lys Asp Arg
65              70                  75                  80

Lys Met Val Ile Phe Pro Asn Asn Phe Glu Ile Thr Asp Lys Asn Leu
                85                  90                  95

Leu Glu Tyr Tyr Leu Lys Thr Leu Glu Glu Pro Leu His Pro Gln Asp
            100                 105                 110

Thr Ile Tyr Arg Asn Arg Phe Ile Tyr Lys Val Pro Asp Val Ser Tyr
        115                 120                 125

Thr Ser Gln Thr Ile Asn Leu Phe Ser Gly Leu Ser Gln Asn Ser Gln
130                 135                 140

Ser Ser Lys Cys Glu Asp Leu Ser Ser Ser Tyr Ser Phe Asp Val Ser
145                 150                 155                 160

Gly Pro Gln Asn Lys Asn Cys Asp Leu Tyr Lys Val Leu Gly Lys Phe
                165                 170                 175

Leu Asn Asp Asn Ser Glu Tyr Phe Gln Glu Ile Ser Pro Leu Phe Pro
            180                 185                 190

Lys Leu Lys Glu Met Leu Val Lys Glu Ile Glu Lys His Trp Phe
        195                 200                 205

Gln Leu Ile Gly Ser Ser Val Trp Leu Glu Gln Tyr Gly Val His Leu
210                 215                 220

Met Thr Ser Arg Ile Phe Tyr Ser Ser Thr Gly Asp Lys Val Lys Pro
225                 230                 235                 240

Val Val Ser Leu Thr Tyr Val Gln Val Phe Asp His Glu Trp Arg Glu
            245                 250                 255

Ile Glu Asn Val Glu Leu Ile Val Pro Asp Gly Glu Gly Lys Tyr Lys
        260                 265                 270

Pro Met Thr Tyr Pro Thr Phe Leu Pro Met Ser Val Tyr His Asn Glu
            275                 280                 285

Lys Gln Gln Gln Gly Arg Phe Tyr Gly Val Glu Asp Pro Arg Ile Thr
        290                 295                 300

Leu Val Arg Asn Lys Leu Gly Tyr Asp Glu Pro Ile Val Tyr Asn
305                 310                 315                 320

Ser His His Arg Lys Ile Thr Asp Ala Lys Ser Asp Asn Asp Gly Glu
            325                 330                 335

Ser Asn Ile His Phe Lys Ala Tyr Arg Ser Ile Phe Met Ala Trp Leu
            340                 345                 350

Trp Gln Asn Gln Lys Gly Lys Asn Asn Val Glu Glu Ile Glu Thr Gly
        355                 360                 365

Lys Met Lys Asn Arg Val Tyr Val Lys Ser Lys Glu Leu Ile Lys Pro
370                 375                 380

Asn Asn Lys Arg Glu Asp Lys Glu Lys Asn Trp Ala Pro Phe Ile Asn
385                 390                 395                 400

Tyr Gln Gln Arg Leu Gln Gln Gly Phe Asp Ser His Val Tyr Phe Met
            405                 410                 415
```

```
Tyr Gln Phe Gln Asp Leu Lys Ile Leu Lys Cys Ser Leu Leu Asp Glu
                420                 425                 430

Glu Asp Cys Val Trp Glu Tyr Gln Phe Asn Asp Lys Asn Gly Ala Gly
            435                 440                 445

Arg Leu Arg Gly Gly Thr Glu Leu Val Asn Ile Asn Gln Leu Leu Thr
        450                 455                 460

Thr Phe Asp His Pro Glu Ile Lys Arg Val Lys Asp Leu Met Pro Gln
465                 470                 475                 480

Asn Arg Glu Ile Trp Ile Gly Val Ala Arg Ala Leu Glu Lys Cys
                485                 490                 495

Gly Cys Gly Asp Lys Met Tyr Arg Pro Asn Ile Val Ile Leu Ile Lys
            500                 505                 510

Asp Gly Asp Asp Gln Tyr Arg Leu Ser His Val Ser Pro Phe Val Gly
        515                 520                 525

Leu Gly Ile Leu Ile Leu Pro Trp Trp Pro Asp Lys Gly Leu Cys Asp
    530                 535                 540

Gly Lys Asn Leu Ile Ile Pro Asn Gly Ile Ser Ser Trp His Leu Asn
545                 550                 555                 560

Lys Asp Glu Asp Asn Ser Val Gln Asp Tyr Leu Thr Leu Ser Ile Ser
                565                 570                 575

Arg Ala Asp Ser Thr Val Asp Leu Leu His Ile Lys Gly Leu Leu Lys
            580                 585                 590

Ser Ile Leu Phe Asp Asp Pro Asn Ser Lys Leu Leu Glu Leu Asn Asp
        595                 600                 605

Tyr Gly Phe Asn Asn Lys Asn Ile Glu Cys Ala Val Lys Ser Ser Asp
    610                 615                 620

Ala Phe Cys Lys Lys Tyr Gly Ser Glu Tyr Lys Leu Asn Asn Asn Lys
625                 630                 635                 640

Glu Glu Asp Lys Ala Asn Gly Asn Gly Lys Gly Ser Ser Ser
                645                 650

<210> SEQ ID NO 19
<211> LENGTH: 646
<212> TYPE: PRT
<213> ORGANISM: Candida albicans

<400> SEQUENCE: 19

Met Gly Asn Tyr Lys Pro Ser Ile Lys Gln Tyr Val Val Thr Val Lys
1               5                   10                  15

Ala Ile Lys Ser Ser Gln Phe Gly Arg Leu Gly Ile Cys Ala Val Val
                20                  25                  30

Leu Leu Phe Val Leu Gly Tyr Pro Phe Tyr Phe Ile Ser Asn Asn Pro
            35                  40                  45

Phe Asp Thr Ser Ile Arg Tyr Gln Tyr Val Asp Pro Tyr Asn Asp Thr
        50                  55                  60

Thr Arg Lys Tyr Thr Thr Ile Glu Lys Gln His Thr Asp Ile Gly Gly
65                  70                  75                  80

Asn Gly Thr Thr Ile Leu Tyr Pro Lys Asn Leu Gln Leu Asp Gln Thr
                85                  90                  95

Ala Leu Ser Gln Leu Leu Asn Thr Thr Glu Thr Thr Asn Pro Phe Val
            100                 105                 110

Gln Tyr Ile Gly Asn Ser Ser Ser Ile Ala Phe Ser Gln Leu Asn Gln
        115                 120                 125

Thr Leu Val Asn His Ser Ile Gln Val Phe Asp Pro Phe Ser Asn Ser
    130                 135                 140
```

```
Asp Asn Cys Ser Asp Leu Met Thr Glu Thr Gln Leu Thr Ile Ser Gln
145                 150                 155                 160

Asn Ile Ile Ile Lys Glu Ser Phe Glu Ile Met Val Lys Arg Leu Met
                165                 170                 175

His Gln Leu Asp Thr Glu Pro Ala Phe Lys Glu Leu Ala Pro Phe Phe
            180                 185                 190

Gln Asn Lys Leu Ser Leu His Leu Arg Met Arg Ser Tyr His Lys His
        195                 200                 205

Phe Tyr Lys Phe Ala Arg Thr Ser Val Trp Leu Lys Asp Tyr Gly Val
    210                 215                 220

His Leu Met Ile Ser Arg Val Ile Tyr Ser Gln Lys Gly Lys Lys Gly
225                 230                 235                 240

Asp Pro Gln Ile Ser Leu Leu Tyr Thr Gln Leu Tyr Asp Thr Asn Trp
                245                 250                 255

Gln Glu Leu Thr Asn Thr Asp Leu Leu Val Ser Met Gln Asp Ile Thr
                260                 265                 270

Gly Glu Tyr Lys Leu Glu Lys Leu Gln Phe Pro Arg Phe Leu Pro Met
            275                 280                 285

Pro Phe Tyr Tyr Asn Pro Lys Leu Thr Lys Gly Arg Trp Tyr Gly Pro
        290                 295                 300

Glu Asp Ala Arg Ile Met Leu Val Lys Asn Gln Leu Asp Met Glu Glu
305                 310                 315                 320

Pro Met Val Ile Tyr Asn Ser Tyr His Arg Gln Ile Ala Asn His Thr
                325                 330                 335

Thr Thr Gly Lys Thr Asp Gly Ser Val Glu Leu Asn Phe Glu Phe Tyr
            340                 345                 350

Arg Ser Met Phe Val Gly Trp Pro Phe Arg Tyr Gln Leu Gly Lys Ser
        355                 360                 365

Asn Thr Asp Gly Phe Val Asp Asp Arg Phe Asp Asn Val Lys Phe Thr
    370                 375                 380

Arg Val Ala Glu Leu Lys Ile His Asn Gln Thr Arg Ala Ser Ile Glu
385                 390                 395                 400

Lys Asn Trp Thr Pro Phe Val Asp Pro Ser Glu Arg Asp Pro Glu Asp
                405                 410                 415

Lys Ser Leu Tyr Ile Val Tyr Gln Trp Asp Lys Leu Arg Ile Leu Lys
                420                 425                 430

Cys Asp Ile Ser Asn Leu Val Thr Asp Asp Gly Phe Ile His Tyr Ser
            435                 440                 445

Ala Cys Arg Phe Lys Gln Asp Thr Lys His Asp Glu Met Glu Lys Val
        450                 455                 460

Gly Pro Ile Arg Gly Gly Thr Lys Leu Ile Pro Thr Ile Asn Asn
465                 470                 475                 480

Lys Gln Leu Trp Val Gly Phe Leu Arg Thr His Ile Asp Lys Cys Gly
                485                 490                 495

Cys Gly Lys Ala Met Asp Arg Pro Asn Met Gly Val Leu Gln Arg Thr
            500                 505                 510

Asp Met Gly Thr Phe Gln Val Ala Tyr Leu Ser Ser Tyr Ile Ser Phe
        515                 520                 525

Asn Ile Ala Val Pro Gly Trp Lys Thr His Glu Ile Gln Cys Gly Lys
    530                 535                 540

Arg Asp Pro Asn Val Leu Ile Pro Asn Gly Ile Ser Asn Trp Glu Val
545                 550                 555                 560
```

```
Ala Thr Ile Asp Gly Ile Glu Arg Asp Val Leu Thr Met Thr Leu Ser
            565                 570                 575

Ala Ala Asp Glu Asp Asn Ile Leu Met Asp Ile His Gly Leu Lys Thr
            580                 585                 590

Val Ile Lys Asn Leu Ile Thr Asn Gln Lys His Gly Asn Glu Phe Asn
            595                 600                 605

Ser Asp Ser Val Gln Met Lys Cys Val Val Ala Tyr Ser Ile Glu Phe
            610                 615                 620

Cys Arg Ala Tyr Gly Glu Gln Ala Arg Leu Gly Leu Thr Gly Gly
625                 630                 635                 640

Trp Leu Pro Ser His Asn
                645

<210> SEQ ID NO 20
<211> LENGTH: 612
<212> TYPE: PRT
<213> ORGANISM: Candida albicans

<400> SEQUENCE: 20

Met Val Gln Lys Gln Tyr Arg Phe Ala Pro Lys Ser Ile Phe Thr Phe
1               5                   10                  15

Val Phe Leu Cys Phe Val Ala Ile Val Val Ile Ile Ser Thr Ser Ser
            20                  25                  30

Leu Val Gln Val Glu Glu Ser Leu Asp Pro Ile Glu Val Ser Asp Glu
        35                  40                  45

Ile Lys Lys His Asp Arg Lys Val Val Ile Phe Pro Ser Asn Phe Gln
    50                  55                  60

Ser Ala Asn Asn Lys Leu Ala Asp Phe Leu Thr Glu Ala Phe Gly Gln
65                  70                  75                  80

Arg Leu Asn Lys Gly Asp Ile Val Tyr Lys Asn Arg Asp Thr Tyr Glu
                85                  90                  95

Leu Pro Gln Thr Val Tyr Thr Trp Asn Thr Ile Asp Leu Phe Gln Ser
            100                 105                 110

Ile Gly Glu Lys Asp Asn Leu Lys Cys Glu Lys Ile Pro Leu Asn Phe
        115                 120                 125

Glu Ile Ser Lys Ile Tyr Asn Lys Asn Ala Asp Leu Tyr Lys Ile Leu
    130                 135                 140

Arg Asp Phe Lys Asn Glu Asn Ser Phe Tyr Tyr Lys Glu Val Ser Val
145                 150                 155                 160

Phe Phe Pro Asp Leu Gly Lys Gln Leu Arg Glu Arg Thr Ile Glu Lys
                165                 170                 175

His Trp Phe Gln Leu Ile Gly Ser Ser Val Trp Leu Glu Gln Tyr Gly
            180                 185                 190

Val His Leu Met Ile Ser Arg Val Ile Tyr Thr Lys Thr Gly Asn Lys
        195                 200                 205

Val Gln Pro Val Ile Ser Leu Ser Tyr Val Gln Ala Phe Asp Arg Asn
    210                 215                 220

Trp Thr Glu Leu Lys Asn Val Thr Leu Val Val Pro Asp Ser Gly Lys
225                 230                 235                 240

Ala Lys Phe Lys Thr Val Ser Tyr Pro Ser Phe Ile Pro Ile Pro Val
                245                 250                 255

Tyr His Asn Val Asn Gln Gln Arg Gly Lys Phe Tyr Gly Val Glu Asp
            260                 265                 270

Pro Arg Ile Met Leu Val Lys Asn Lys Glu Gly Tyr Glu Glu Pro Leu
        275                 280                 285
```

```
Ile Val Tyr Asn Ser Phe Asn Arg Ser Pro Pro Asn Ala Asn Tyr Leu
    290                 295                 300

Glu Glu Ile Lys Asn Leu Val Lys Leu Asp Thr Tyr Arg Ser Ile Phe
305                 310                 315                 320

Met Ala Trp Ile Trp Arg Thr Gln Leu Gly Lys Ser Asn Val Gly Ser
                325                 330                 335

Ser Leu Pro Asp Leu Ala Thr Thr Asp His Lys Tyr Val Lys Val
                340                 345                 350

Lys Glu Leu Ser Leu Pro Asn Lys Lys Arg Pro Lys Thr Glu Lys Asn
                355                 360                 365

Trp Thr Pro Phe Val Ile Tyr Glu Asp Gln Lys Lys Gln Gly Tyr Asp
    370                 375                 380

Ser His Leu Tyr Phe Ile Tyr Ser Phe Gln Asp Leu Ser Ile Leu Lys
385                 390                 395                 400

Cys Ser Leu Trp Asp Ala Gly Asn Cys Ile Trp Glu Tyr Arg Met Asn
                405                 410                 415

Asn Lys Lys Thr Lys Ile Ser Glu Leu Arg Gly Gly Thr Glu Leu Met
                420                 425                 430

Asn Val Asn Gln Leu Leu Asp Lys Tyr Asn Phe Ala Gly Leu Glu Thr
            435                 440                 445

Val Lys Asp Gln Phe Lys Gly Lys Glu Val Trp Ile Ser Phe Ala Arg
    450                 455                 460

Ala Ala Leu Ser Lys Cys Gly Cys Gly Ser Lys Met Tyr Arg Pro Asn
465                 470                 475                 480

Phe Thr Val Leu Val Lys Gln Gly Gly Arg Phe Gln Leu Ser Phe Val
                485                 490                 495

Ser Ser Tyr Met Asp Phe Gly Val Pro Ile Leu Pro Trp Ala Lys Gly
                500                 505                 510

Lys Gly Leu Cys Asn Gly Lys Asn Leu Leu Ile Pro Asn Gly Ile Ser
                515                 520                 525

Asn Trp Val Leu Ala Lys Asp Glu Gly Gly Phe Gln Asp Tyr Met
    530                 535                 540

Thr Leu Ser Leu Ser Arg Ser Asp Ser Thr Val Asp Ile Ile His Met
545                 550                 555                 560

Lys Gly Ile Leu Lys Ser Ile Leu Ser Glu Tyr Leu Leu Gln Thr Asn
                565                 570                 575

Arg Asp Val Leu Asn Asn Asn Ala Ile His Cys Ala Leu Leu Glu Ser
                580                 585                 590

Glu Ser Tyr Cys Lys Ser Tyr Ala Glu Asn Tyr Arg Ala His Leu Lys
                595                 600                 605

Arg Trp Gln Asn
    610

<210> SEQ ID NO 21
<211> LENGTH: 650
<212> TYPE: PRT
<213> ORGANISM: Candida albicans

<400> SEQUENCE: 21

Lys Leu Glu Met Ser Ser Tyr Leu His Lys Val Pro Asn Thr Gly Ile
1               5                   10                  15

Thr Asn Leu Ser Asn Ser Lys Ser Ile Val Phe Ile Met Phe Cys Ala
                20                  25                  30

Thr Leu Leu Phe Ile Ile Thr Ser Ser Arg Tyr Leu Thr Gly Ser Glu
```

```
                35                  40                  45
Ser Leu Gly Gln Ile Pro Ser Glu Ile Pro Lys Ser Glu Gln Leu
 50                  55                  60

Asn Glu Glu Leu Ser Gln Gln Ile Asn Ser Lys Leu His Lys Leu Ala
 65                  70                  75                  80

Ser Phe Asp Lys Phe Asn Ser Phe Pro Leu Leu Asn Lys His Met Lys
                 85                  90                  95

Asp Asp Ile Tyr Gly Leu Met Thr Leu Glu Thr Phe Thr Asp Pro Leu
                100                 105                 110

Pro Tyr Leu Glu Asn Tyr Asn Glu Glu Tyr Ser Gln Gln Asn Tyr
            115                 120                 125

Pro Ile Cys Ser Glu Lys Leu Met Phe Pro Ser Lys Ile Lys Leu Thr
            130                 135                 140

Lys Gln Gln Tyr Leu Pro Ala Asp Leu Gln Gln Phe Leu Gly Val Leu
145                 150                 155                 160

Asn Asn Met Arg Pro Tyr His Asp Met Val Glu Lys Ala Lys Ala Tyr
                165                 170                 175

Phe Ile Ser Asp Leu Arg Glu Glu Lys Lys Trp Phe Arg Phe Ala Gly
            180                 185                 190

Ser Ser Ile Trp Leu Pro Gln Phe Gln Cys His Tyr Met Val Ser Arg
            195                 200                 205

Tyr Leu Tyr Ser Pro Asn Gly Val Ala Asn His Ala Phe Ala Ser Phe
            210                 215                 220

Leu Tyr Ile Gln Leu Phe Asp Ser Asp Trp Lys Glu Leu Pro Ser His
225                 230                 235                 240

Thr Thr Leu Asp Ile Pro Phe Glu Gln Thr Glu Ala Asn Ser Ile Phe
                245                 250                 255

Lys Ile Phe Lys Pro Lys Gln Lys Tyr Ala Asn Phe Arg Asn Ser Thr
                260                 265                 270

Tyr Pro Gln Ile Leu Pro Ile Pro Phe Asp Tyr Lys Leu Pro Ile Glu
            275                 280                 285

Thr Lys Lys Tyr Tyr Gly Pro Glu Asp Pro Arg Ile Leu Leu Arg
            290                 295                 300

Ser Asn Pro Leu Gly Phe Asp Glu Pro Leu Ile Val Phe Asn Met Lys
305                 310                 315                 320

Gly Leu Lys Leu Thr Lys Arg Val Met Tyr Ser Tyr Leu Pro Phe Ser
                325                 330                 335

Asn Thr Leu Lys Leu Leu Lys Lys Arg Arg Glu Pro Phe Ala Asn Ile
            340                 345                 350

Glu Lys Asn Trp Thr Pro Phe Lys Ser Val Ala Gln Pro Ser Lys Thr
            355                 360                 365

Gln Thr Thr Ile His Phe Ile Tyr Ser Met Ile Pro Leu Glu Val Leu
            370                 375                 380

Ala Cys Asp Ile Asp Ser Gly Leu Cys Asp Ile Leu Gln Lys Pro Ala
385                 390                 395                 400

Lys His Asp Phe Asn Tyr Val Gly Gly Leu Arg Gly Gly Thr Gln Leu
                405                 410                 415

Val Ser Leu Pro Leu Asn Glu Thr Ile Pro Ser Glu Ile Arg Ala Lys
            420                 425                 430

Leu Pro Ile Pro Lys Asn Arg Gln Val Tyr Ile Gly Trp Ala Arg Thr
            435                 440                 445

His Leu Asn Asn Cys Gly Cys Gly Asp Ser Met Tyr Arg Pro Asn Phe
450                 455                 460
```

```
Ile Thr Leu Val Glu Asp Tyr Asp Val Thr Asp Lys Tyr Tyr
465                 470                 475                 480

Lys Ile Gly Asp Ile Ser Gly Tyr Phe Asp Phe Ala Ala Lys Ile Glu
                485                 490                 495

Pro Trp Ser Lys Gln Val Leu Asp Glu Gly Asn Leu Tyr Glu Lys
            500                 505                 510

Ala Glu Gln Cys Gln Gly Arg Asn Val Leu Ile Pro Asn Ser Ile Ala
                515                 520                 525

Tyr Trp Asp Val Gly Ser Ile Lys Leu Ala Gly Thr Glu Tyr Gln Lys
530                 535                 540

His Asp Phe Lys Asp Met Phe Ser Ser Gly Lys Val Ser Asp Phe Asn
545                 550                 555                 560

Ala Asn Glu Ile Val Phe Asn Asp Tyr Met Gly Val Thr Leu Ser Ser
                565                 570                 575

Ala Asp Arg Asp Val Ser Ile Val His Val Lys Gly Leu Leu Asn Tyr
                580                 585                 590

Ile Leu Gln Leu Pro Ser Leu Val Asp Asp Ser Leu Val Ile Asn Lys
                595                 600                 605

Glu Trp Thr Phe Gln Lys Lys Gly His Asp Leu Asn Val Arg Cys Ala
610                 615                 620

Met Ile Ala Ser Lys Glu Tyr Cys Lys Ser Tyr Ala Ile Lys Gln Gly
625                 630                 635                 640

Val Lys Ile Asp Glu Lys Ser Glu Glu Thr
                645                 650

<210> SEQ ID NO 22
<211> LENGTH: 590
<212> TYPE: PRT
<213> ORGANISM: Candida albicans

<400> SEQUENCE: 22

Met Leu Ile Val Phe His Ser Phe Phe Ser Phe Phe Pro Phe Leu Thr
1               5                   10                  15

Phe Phe Phe Leu Tyr Phe Ile Asn Arg Asp Leu Pro Ile Ile Ile Lys
                20                  25                  30

Asp Ile Leu Leu Ile Glu Asp Ser Glu Met Phe Glu Ser Asp Leu Ser
                35                  40                  45

Phe Tyr Ser Ala Leu Leu Ile Leu Cys Cys Pro Ile Ser Ile Val Phe
            50                  55                  60

Phe Lys Lys Phe Pro Ile Lys Gly Tyr Thr Gly Ala Asn Lys Val Ser
65              70                  75                  80

Leu Phe Leu Gln Cys Leu Ile Ala Ile Leu Asn Leu Asn Ile Leu Tyr
                85                  90                  95

Ser Phe Ile Asn Ser Leu Thr Ile Thr Leu Gly His Asp Gly Ser Ser
                100                 105                 110

Ala Asn Thr Leu Thr Ile Asp Pro Ile Thr Thr Gln Gln Gln Gly
            115                 120                 125

His Val Asp Tyr Thr Pro Ile Lys Val Ser Gly Tyr Thr Phe Lys Asn
            130                 135                 140

Gln Val Ala Thr Lys Asn Leu Gln Cys Asp Ser Ile Val Tyr Asp Gln
145                 150                 155                 160

Asp Leu Asp Leu Gln Val Ser Gln Ala Val Asp Leu Asn Lys Pro Glu
                165                 170                 175

Asp Leu Lys Phe Phe Arg Asp Lys Leu Asn Glu Leu Arg Ser Leu Asn
```

```
                180                 185                 190
Asn Ile Tyr Asp Leu Phe Phe Gln Asp Asn Glu Asp Glu Val Glu Glu
                195                 200                 205

Ser Ile Leu Glu Arg Lys Trp Tyr Lys Phe Cys Gly Ser Ala Val Trp
210                 215                 220

Leu Asp Lys Tyr Gly Val Tyr Phe Met Val Asn Arg Ile Ala Tyr Ser
225                 230                 235                 240

Lys Lys Gly Thr Arg Asn Asn Pro Thr Ile Ser Val Leu Ala Gly Gln
                245                 250                 255

Val Phe Asp Lys Asn Trp Ile Glu Leu Thr Gly Lys Lys Phe Pro Phe
                260                 265                 270

Ser Gly Leu Glu Phe Pro Thr Ile Leu Pro His Tyr Ile Asp Glu Gly
                275                 280                 285

Lys Glu Ala Glu Lys Val Ile Leu Gly Ala Glu Asp Pro Arg Val Ile
                290                 295                 300

Leu His Glu Tyr Thr Asn Glu Asn Gly Ile Arg Ile Gln Glu Pro Leu
305                 310                 315                 320

Ile Ala Phe Asn Ala Leu Ser Thr Glu Val Asp Trp Lys Arg Ala Met
                325                 330                 335

His Ile Tyr Arg Pro Leu His Asp Pro His Arg Ile Ile Arg Leu Ser
                340                 345                 350

Ile Glu Asn Tyr Ala Pro Arg Glu Lys Glu Lys Asn Trp Ala Pro Phe
                355                 360                 365

Ile Asp Gly Asn Asn Leu Asn Phe Val Tyr Asn Phe Pro Leu Arg Ile
                370                 375                 380

Leu Arg Cys Asn Ile Asn Asn Gly Asp Cys Gln Lys Val Ser Gly Pro
385                 390                 395                 400

Asp Phe Asn Asp Lys Ser His Glu Asn Ala Gly Lys Leu Arg Gly Gly
                405                 410                 415

Thr Asn Leu Val Glu Ile Pro Ser Gln Ser Leu Pro Lys His Leu Arg
                420                 425                 430

Ser Arg Lys Tyr Trp Phe Gly Ile Ala Arg Ser His Ile Thr Asp Cys
                435                 440                 445

Gly Cys Val Gly Glu Leu Tyr Arg Pro His Leu Ile Leu Ile Ser Arg
450                 455                 460

Asn Lys Lys Ser Asp Gln Tyr Glu Leu Asn Tyr Val Ser Asp Leu Ile
465                 470                 475                 480

Asp Phe Asn Val Asn Pro Glu Pro Trp Thr Pro Gly Lys Thr Thr Cys
                485                 490                 495

Ser Asp Gly Lys Ser Val Leu Ile Pro Asn Ser Val Ala Phe Ile Lys
                500                 505                 510

Asp Asp Tyr Met Ser Val Thr Phe Ser Glu Ala Asp Lys Thr Asn Lys
                515                 520                 525

Leu Ile Asn Ala Lys Gly Trp Leu Thr Tyr Ile Thr Lys Met Leu Glu
                530                 535                 540

Phe Thr Gln Glu Arg Leu Lys Asp Glu Ser Ser Asp Pro Val Leu Glu
545                 550                 555                 560

Ser Arg Leu Leu Ser Lys Cys Ser Thr Phe Leu Ala Gln Gln Tyr Cys
                565                 570                 575

Ala Leu Ser Lys Asp Thr Met Gly Trp Asp Lys Leu Ser Arg
                580                 585                 590

<210> SEQ ID NO 23
```

<211> LENGTH: 684
<212> TYPE: PRT
<213> ORGANISM: Candida albicans

<400> SEQUENCE: 23

```
Met Asp Lys Phe Ile Gln Ser Phe Ser His Gln Tyr Leu Asp Ser Ser
1               5                   10                  15

Ser Ser Leu Lys Leu Thr Ala Arg Arg Lys Arg Lys Leu Thr Ile Leu
            20                  25                  30

Gly Leu Phe Leu Phe Ser Leu Ile Ser Leu Met Ile Ile Ile Ser Tyr
        35                  40                  45

Ser Asn Asn Asn Ile Leu Pro Gly Leu Ser Gly Ile Ser Ile Ser Ser
    50                  55                  60

Thr Phe Ser Asp Tyr Tyr Ser Asn Pro Lys Gln Gln Asn Lys Phe Glu
65                  70                  75                  80

Gln Gln Ile Gln Asp His Gln Thr Thr Lys Lys Gly Lys Arg Thr Ile
                85                  90                  95

Ile Phe Pro Asn Asn Phe Asn His Val His Asp His Lys Gly Ser Tyr
            100                 105                 110

Met Met Lys Asp Ser Glu Leu Val Lys Tyr Tyr Val Glu Thr Met Glu
        115                 120                 125

Gln Ala Leu Asp Pro Glu Asp Leu Ile Tyr Arg Asn Arg Phe Thr Tyr
    130                 135                 140

Lys Leu Pro Asn Ile Pro Tyr Thr Glu Gln Lys Ile Glu Met Phe Ser
145                 150                 155                 160

Asp Gly Gly Gly Gly Gly Asp Thr Ser Asp Ser Asn Thr Asp Met
                165                 170                 175

Cys Pro Lys Leu Ser Thr Thr Ile Lys Val Glu Ala Ser Pro Ala Met
            180                 185                 190

Asn Lys Asn Gly Asp Leu Lys Lys Ile Leu Lys Thr Phe Leu Gln Glu
        195                 200                 205

Asp Ser Phe Tyr Tyr Arg Glu Leu Ser Pro Phe Phe Pro Asp Leu Lys
    210                 215                 220

Lys His Phe Asp Glu Asp Thr Ile Asp Lys His Trp Tyr Gln Phe Ile
225                 230                 235                 240

Gly Ser Thr Val Trp Leu Glu Gln Tyr Gly Val His Leu Met Val Ser
                245                 250                 255

Arg Ile Ile Tyr Thr Glu Lys Asp Gln Gly Ser Pro Lys Phe Ser Leu
            260                 265                 270

Ala Tyr Leu Gln Val Phe Asp Arg Asn Trp Lys Glu Leu Asp Asn Val
        275                 280                 285

Glu Leu Ile Val Pro Asp Pro Glu Asn Ile Ser Thr Thr Asn Asn Lys
    290                 295                 300

Asn Lys Asn Lys Lys Pro Tyr Gly Tyr Lys Ser Val Leu Tyr Pro Thr
305                 310                 315                 320

Ile Ala Pro Ile Pro Val Tyr His Asn Ser Lys Gln Thr Gly Gly Arg
                325                 330                 335

Phe Tyr Gly Ile Glu Asp Pro Arg Ile Val Leu Ile Lys Thr Arg His
            340                 345                 350

Gly Tyr Glu Glu Pro Val Leu Ile Tyr Asn Ser His His Arg Lys Ile
        355                 360                 365

Ser Glu Lys His Phe Asp Asn Asp Gln Glu Gly Lys Ile Asn Phe Asn
    370                 375                 380

Asn Tyr Arg Ser Leu Phe Ile Gly Trp Ile Trp Gln Thr Gln Leu Gly
```

-continued

```
385                 390                 395                 400
Lys Ile His Leu Glu Glu Leu Pro Asn Asn Glu Phe Lys Lys Asn Glu
                405                 410                 415
Tyr Ile Lys Ile Lys Glu Phe Val Lys Pro Asn Asn Asn Arg Gly Arg
                420                 425                 430
Thr Glu Lys Asn Trp Ala Leu Phe Ile Asn Tyr Asn Gln Arg Leu Asn
                435                 440                 445
Gln Gly Phe Asp Ser His Val Tyr Phe Ala Asn Gln Leu Lys Asn Leu
            450                 455                 460
Lys Ile Leu Lys Cys Ser Ile Leu Asn Asp Asn Asp Asp Cys Glu
465                 470                 475                 480
Trp Glu Phe Gln Met Asp Asp Tyr Glu Asp Ala Gly Val Leu His Gly
                485                 490                 495
Gly Thr Glu Leu Ile Asn Ile Asn Gln Leu Leu His Gln Tyr Asp Tyr
                500                 505                 510
Pro Glu Leu Asn Ser Ile Lys Asp Leu Ile Pro Asn Gly Arg Glu Tyr
                515                 520                 525
Trp Val Gly Phe Ala Arg Ala Ser Leu Lys Asn Cys Gly Cys Gly Ser
        530                 535                 540
Arg Met Tyr Arg Pro Asn Leu Ile Val Leu Met Lys Asp Gly Lys Asn
545                 550                 555                 560
Tyr Lys Phe Ala Tyr Val Ser Ser Phe Val Gly Leu Gly Ile Glu Ile
                565                 570                 575
Leu Pro Trp Tyr Leu Asp Lys Gly Leu Cys Glu His Tyr Asn Leu Ile
                580                 585                 590
Ile Pro Asn Gly Ile Ser Ser Trp Thr Ile Glu Lys Asp Leu His Gln
            595                 600                 605
Lys Glu Lys Asp Lys Gln Val Met Asp Tyr Met Ala Phe Thr Ile Ser
        610                 615                 620
Arg Arg Asp Ala Thr Val Asp Val Val Tyr Val Lys Gly Leu Leu Lys
625                 630                 635                 640
Ala Leu Phe Thr Asp Ser Ser Ser Ser Lys His Leu Leu Ala Val Glu
                645                 650                 655
Gln Thr Gly Phe Lys Ser Val Thr Asn Val Asp Cys Ala Leu Lys Asn
                660                 665                 670
Ser Glu Lys Phe Cys Lys Ile Tyr Gly Glu Thr Phe
            675                 680
```